United States Patent [19]

McDonagh et al.

[11] Patent Number: 5,837,536
[45] Date of Patent: Nov. 17, 1998

[54] EXPRESSION OF HUMAN MULTIDRUG RESISTANCE GENES AND IMPROVED SELECTION OF CELLS TRANSDUCED WITH SUCH GENES

[75] Inventors: Kevin T. McDonagh, Silver Spring; Arthur Nienhuis, Bethesda; Paul Tolstoshev, Potomac, all of Md.

[73] Assignees: Genetic Therapy, Inc., Gaithersburg, Md.; The United States of America as represented by the Department of Health and Human Services, Washington, D.C.

[21] Appl. No.: 583,276

[22] Filed: Jan. 5, 1996

Related U.S. Application Data

[63] Continuation of Ser. No. 332,444, Oct. 31, 1994, abandoned, which is a continuation of Ser. No. 887,712, May 22, 1992, abandoned.

[51] Int. Cl.$^6$ .............................. C12N 5/22; C12N 15/12; C12N 15/86
[52] U.S. Cl. ....................... 435/325; 536/23.5; 435/69.1; 435/320.1
[58] Field of Search ..................... 536/23.1; 435/69.1, 435/320.1, 240.2, 325

[56] References Cited

U.S. PATENT DOCUMENTS

| | | | |
|---|---|---|---|
| 4,912,039 | 3/1990 | Riordan | 435/69.1 |
| 5,166,059 | 11/1992 | Pastan et al. | 435/69.7 |
| 5,175,099 | 12/1992 | Wills | 435/69.7 |
| 5,192,553 | 3/1993 | Boyse et al. | 424/529 |
| 5,198,344 | 3/1993 | Croop et al. | 435/69.1 |
| 5,206,352 | 4/1993 | Roninson et al. | 536/24.31 |

FOREIGN PATENT DOCUMENTS 2-100680   4/1990   Japan .

OTHER PUBLICATIONS

Safa, et al., *Proc. Nat. Acad. Sci.,* vol. 87, pp. 7225–7229 (1990).
Weinstein, et al. "Multidrug Resistance Gene Product (P–Glycoprotein) in Normal Tissue and Tumors," *Advances in Pathology and Laboratory Medicine,* Mosby Yearbook, Inc. (1991).
Schinkel, et al., *Cancer Research,* vol. 51, pp. 2628–2635 (May 15, 1991).
Devine, et al., *Proc. Nat. Acad. Sci.,* vol. 89, pp. 4565–4568 (May 1992).
Pastan, et al., *FASEB J.,* vol. 5, pp. 2523–2528 (1991).
Chaudhary, et al., *Cell,* vol. 68, pp. 85–94 (Jul. 12, 1991).
Devine et al. Mar. 5, 1991. J. Biol. Chem. 266(7):4545–4555.
Chaudhary et al. 1991. Cell 66:85–94.
Pastan et al. 1991. The FASEB J. 5:2523–2528.
Aebi et al. 1986. Cell 47:555–565.
Ohshima et al. 1987. J. Mol. Biol. 195:247–259.

*Primary Examiner*—Robert A. Wax
*Assistant Examiner*—Karen Cochrane Carlson
*Attorney, Agent, or Firm*—Elliot M. Olstein; Raymond J. Lillie

[57] ABSTRACT

A DNA sequence for a human mdr1 gene, which encodes p-glycoprotein, wherein at least one base in a splice region of the DNA encoding p-glycoprotein is changed. Such a mutation prevents truncation of the p-glycoprotein upon expression thereof. There is also provided a method of identifying cells which express the human mdr1 gene in a cell population that has been transduced with an expression vehicle including a human mdr1 gene. The method comprises contacting the cell population with a staining material, such as rhodamine 123, and identifying cells which express the human mdr1 gene based on differentiation in color among the cells of the cell population. This method has allowed identification of retroviral producer clones facilitate mdr gene transfer into primary cells. Repopulating hematopoietic stem cells have been genetically engineered with the human mdr1 gene.

21 Claims, 16 Drawing Sheets

SEQUENCE OF THE MULTIPLE CLONING SITE IN THE pGI PLASMID

| 1/2 EcoRI | NotI | SnaBI | SalI | BamHI | XhoI | HindIII | ApaI |
|---|---|---|---|---|---|---|---|
| AATTC | GCGGCCGC | TACGTA | GTCGAC | GGATCC | CTCGAG | AAGCTT | GGGCCC |
| G | CGCCGGCG | ATGCAT | CAGCTG | CCTAGG | GAGCTC | TTCGAA | CCCGGG |

1/2ClaI

AT

TAGC

FIG. 2

FIG. 4A cDNA Sequence of Human mdr1 Gene

```
  1  CCTACTCTAT TCAGATATTC TCCAGATTCC TAAAGATTAG AGATCATTTC
 51  TCATTCTCCT AGGAGTACTC ACTTCAGGAA GCAACCAGAT AAAAGAGAGG
101  TGCAACGGAA GCCAGAACAT TCCTCCTGGA AATTCAACCT GTTTCGCAGT
151  TTCTCGAGGA ATCAGCATTC AGTCAATCCG GGCCGGGAGC AGTCATCTGT
201  GGTGAGGCTG ATTGGCTGGG CAGGAACAGC GCCGGGGCGT GGGCTGAGCA
251  CAGCGCTTCG CTCTCTTTGC CACAGGAAGC CTGAGCTCAT TCGAGTAGCG
301  GCTCTTCCAA GCTCAAAGAA GCAGAGGCCG CTGTTCGTTT CCTTTAGGTC
351  TTTCCACTAA AGTCGGAGTA TCTTCTTCCA AGATTTCACG TCTTGGTGGC
401  CGTTCCAAGG AGGGCGAGGT CGGG
```

```
425  ATG GAT CTT GAA GGG GAC CGC AAT GGA GGA GCA AAG AAG AAG                                  466
     MET Asp Leu Glu Gly Asp Arg Asn Gly Gly Ala Lys Lys Lys

467  AAC TTT TTT AAA CTG AAC AAT AAA AGT GAA AAA GAT AAG AAG                                  508
     Asn Phe Phe Lys Leu Asn Asn Lys Ser Glu Lys Asp Lys Lys

509  GAA AAG AAA CCA ACT GTC AGT GTA TTT TCA ATG TTT CGC TAT                                  550
     Glu Lys Lys Pro Thi Val Ser Val Phe Ser MET Phe Arg Tyr

551  TCA AAT TGG CTT GAT AAG TTG TAT ATG GTG GTG GGA ACT TTG                                  592
     Ser Asn Trp Leu Asp Lys Leu Tyr MET Val Val Gly Thr Leu

593  GCT GCC ATC ATC CAT GGG GCT GGA CTT CCT CTC ATG ATG CTG                                  634
     Ala Ala Ile Ile His Gly Ala Gly Leu Pro Leu MET MET Leu

635  GTG TTT GGA GAA ATG ACA GAT ATC TTT GCA AAT GCA GGA AAT                                  676
     Val Phe Gly Glu MET Thr Asp Ile Phe Ala Asn Ala Gly Asn
```

FIG. 4B

```
677  TTA GAA GAT CTG ATG TCA AAC ATC ACT AAT AGA AGT GAT ATC   718
     Leu Glu Asp Leu MET Ser Asn Ile Thr Asn Arg Ser Asp Ile

719  AAT GAT ACA GGG TTC TTC ATG AAT CTG GAG GAA GAC ATG ACC   760
     Asn Asp Thr Gly Phe Phe MET Asn Leu Glu Glu Asp MET Thr

761  AGG TAT GCC TAT TAC AGT GGA ATT GGT GCT GGG GTG CTG       802
     Arg Tyr Ala Tyr Tyr Ser Gly Ile Gly Ala Gly Val Leu

803  GTT GCT TAC ATT CAG GTT TCA TTT TGG TGC CTG GCA GCT       844
     Val Ala Tyr Ile Gln Val Ser Phe Trp Cys Leu Ala Ala

845  GGA AGA CAA ATA CAC AAA ATT AGA AAA CAG TTT TTT CAT GCT   886
     Gly Arg Gln Ile His Lys Ile Arg Lys Gln Phe Phe His Ala

887  ATA ATG CGA CAG GAG ATA GGC TGG TTT GAT GTG CAC GAT GTT   928
     Ile MET Arg Gln Glu Ile Gly Trp Phe Asp Val His Asp Val

929  GGG GAG CTT AAC ACC CGA CTT ACA GAT GAT GTC TCT AAG ATT   970
     Gly Glu Leu Asn Thr Arg Leu Thr Asp Asp Val Ser Lys Ile

971  AAT GAA GTT ATT GGT GAC AAA ATT GGA ATG TTC TTT CAG TCA   1012
     Asn Glu Val Ile Gly Asp Lys Ile Gly MET Phe Phe Gln Ser

1013 ATG GCA ACA TTT TTC ACT GGG TTT ATA GTA GGA TTT ACA CGT   1054
     MET Ala Thr Phe Phe Thr Gly Phe Ile Val Gly Phe Thr Arg

1055 GGT TGG AAG CTA ACC CTT GTG ATT TTG GCC ATC AGT CCT GTT   1096
     Gly Trp Lys Leu Thr Leu Val Ile Leu Ala Ile Ser Pro Val
```

FIG.4C

```
1097 CTT GGA CTG TCA GCT GCT GTC TGG GCA AAG ATA CTA TCT TCA  1138
     Leu Gly Leu Ser Ala Ala Val Trp Ala Lys Ile Leu Ser Ser

1139 TTT ACT GAT AAA GAA CTC TTA GCG TAT GCA AAA GCT GGA GCA  1180
     Phe Thr Asp Lys Glu Leu Leu Ala Tyr Ala Lys Ala Gly Ala

1181 GTA GCT GAA GAG GTC TTG GCA GCA ATT AGA ACT GTG ATT GCA  1222
     Val Ala Glu Glu Val Leu Ala Ala Ile Arg Thr Val Ile Ala

1223 TTT GGA GGA CAA AAG GAA CTT GAA AGG TAC AAC AAA AAT      1264
     Phe Gly Gly Gln Lys Lys Glu Leu Glu Arg Tyr Asn Lys Asn

1265 TTA GAA GAA GCT AAA AGA ATT GGT ATA AAG AAA GCT ATT ACA  1306
     Leu Glu Glu Ala Lys Arg Ile Gly Ile Lys Lys Ala Ile Thr

1307 GCC AAT ATT TCT ATA GGT GCT TTC TGG ACC TTG ATC TAT GCA  1348
     Ala Asn Ile Ser Ile Gly Ala Phe Trp Thr Leu Ile Tyr Ala

1349 TCT TAT GCT CTG GCC TTC TGG TAT GGA CAA GTA CTC ACT GTA  1390
     Ser Tyr Ala Leu Ala Phe Trp Tyr Gly Gln Val Leu Thr Val

1391 TCA GGG GAA TAT TCT ATT GGG GCT GTT GGA CAG CAG GCA TCT CCA  1432
     Ser Gly Glu Tyr Ser Ile Gly Ala Val Gly Gln Ala Ser Pro

1433 TCT GTA TTA ATT GGG GCT TTT AGT GTT GGA CAG CAG GCA TCT CCA  1474
     Ser Val Leu Ile Gly Ala Phe Ser Val Gly Gln Ala Ser Pro

1475 AGC ATT GAA GCA TTT GCA AAT GCA AGA GGA GCA GCT TAT GAA  1516
     Ser Ile Glu Ala Phe Ala Asn Ala Arg Gly Ala Ala Tyr Glu
```

FIG. 4D

| | | | | | | | | | | | | | | |
|---|---|---|---|---|---|---|---|---|---|---|---|---|---|---|
| 1517 | ATC Ile | TTC Phe | AAG Lys | ATA Ile | ATT Ile | GAT Asp | AAT Asn | AAG Lys | CCA Pro | AGT Ser | ATT Ile | GAC Asp | AGC Ser | TAT Tyr | 1558 |
| 1559 | TCG Ser | AAG Lys | AGT Ser | GGG Gly | CAC His | AAA Lys | CCA Pro | GAT Asp | AAT Asn | ATT Ile | AAG Lys | GGA Gly | AAT Asn | TTG Leu | 1600 |
| 1601 | GAA Glu | TTC Phe | AGA Arg | AAT Asn | GTT Val | CAC His | TTC Phe | AGT Ser | TAC Tyr | CCA Pro | TCT Ser | CGA Arg | AAA Lys | GAA Glu | 1642 |
| 1643 | GTT Val | AAG Lys | ATC Ile | TTG Leu | AAG Lys | GGC Gly | CTG Leu | AAC Asn | CTG Leu | AAG Lys | CTG Val | CAG Gln | AGT Ser | GGG Gly | 1684 |
| 1685 | CAG Gln | ACC Thr | GTG Val | GCC Ala | CTG Leu | GTT Val | GGA Gly | AAC Asn | AGT Ser | GGC Gly | TGT Cys | GGG Gly | AAG Lys | AGC Ser | 1726 |
| 1727 | ACA Thr | ACA Thr | GTC Val | CAG Gln | CTG Leu | ATG MET | CAG Gln | AGG Arg | CTC Leu | TAT Tyr | GAC Asp | CCC Pro | ACA Phr | GAG Glu | 1768 |
| 1769 | GGG Gly | ATG MET | GTC Val | AGT Ser | GTT Val | GAT Asp | GGA Gly | CAG Gln | GAT Asp | ATT Ile | AGG Arg | ACC Thr | ATA Ile | AAT Asn | 1810 |
| 1811 | GTA Val | AGG Arg | TTT Phe | CTA Leu | CGG Arg | GAA Glu | ATC Ile | ATT Ile | GGT Gly | GTG Val | GTG Val | AGT Ser | CAG Gln | GAA Glu | 1852 |
| 1853 | CCT Pro | GTA Val | TTG Leu | TTT Phe | GCC Ala | ACC Thr | ACG Thr | ATA Ile | GCT Ala | GAA Glu | AAC Asn | ATT Ile | CGC Arg | TAT Tyr | 1894 |
| 1895 | GGC Gly | CGT Arg | GAA Glu | AAT Asn | GTC Val | ACC Thr | ATG MET | GAT Asp | GAG Clu | ATT Ile | GAG Glu | AAA Lys | GCT Ala | GTC Val | 1936 |

FIG. 4E

```
1937 AAG GAA GCC AAT GCC TAT GAC TTT ATC ATG AAA CTG CCT CAT  1978
     Lys Glu Ala Asn Ala Tyr Asp Phe Ile MET Lys Leu Pro His
1979 AAA TTT GAC ACC CTG GTT GGA GAG AGA ATG GGG GCC CAG TTG AGT  2020
     Lys Phe Asp Thr Leu Val Gly Glu Arg Gly Ala Gln Leu Ser
2021 GGT GGG CAG AAG AGG CAG ATC GCC ATT GCA CGT GCC CTG GTT  2062
     Gly Gly Gln Lys Arg Gln Ile Ala Ile Ala Arg Ala Leu Val
2063 CGC AAC CCC AAG ATC CTC CTG GAT GAG CTG ACG TCA GCC  2104
     Arg Asn Pro Lys Ile Leu Leu Asp Glu Leu Thr Ser Ala
2105 TTG GAC ACA GAA AGC GCA GTG GTT CAG GTG GCT CTG GAT  2146
     Leu Asp Thr Glu Ser Ala Val Val Gln Val Ala Leu Asp
2147 AAG GCC AGA AAA GGT CGG ACC ATT GTG ATA GCT CAT CGT  2188
     Lys Ala Arg Lys Gly Arg Thr Ile Val Ile Ala His Arg
2189 TTG TCT ACA GTT CGT AAT GCT GAC GTC ATC GCT GGT TTC GAT  2230
     Leu Ser Thr Val Arg Asn Ala Asp Val Ile Ala Gly Phe Asp
2231 GAT GGA GTC ATT GTG GAG AAA GGA AAT CAT GAT GAA CTC ATG  2272
     Asp Gly Val Ile Val Glu Lys Gly Asn His Asp Glu Leu MET
2273 AAA GAG AAA GGC ATT TAC TTC AAA CTT GTC ACA ATG CAG ACA  2314
     Lys Glu Lys Gly Ile Tyr Phe Lys Leu Val Thr MET Gln Phe
2315 GCA GGA AAT GAA GTT GAA TTA GAA AAT GCA GCT GAT GAA TCC  2356
     Ala Gly Asn Glu Val Glu Leu Glu Asn Ala Ala Asp Glu Ser
```

FIG. 4F

| | | | | | | | |
|---|---|---|---|---|---|---|---|
| 2357 AAA | AGT | GAA | ATT | GAT | GCC | TTG | GAA ATG TCT TCA AAT GAT TCA 2398 |
| Lys | Ser | Glu | Ile | Asp | Ala | Leu | Glu MET Ser Ser Asn Asp Ser |
| 2399 AGA | TCC | AGT | CTA | ATA | AGA | AAA | AGA TCA ACT CGT AGG AGT GTC 2440 |
| Arg | Ser | Ser | Leu | Ile | Arg | Lys | Arg Ser Thr Arg Arg Ser Val |
| 2441 CGT | GGA | TCA | CAA | GCC | CAA | GAC | AGA AAG CTT AGT ACC AAA GAG 2482 |
| Arg | Gly | Ser | Gln | Ala | Gln | Asp | Arg Lys Leu Ser Thr Lys Glu |
| 2483 GCT | CTG | GAT | GAA | AGT | ATA | CCT | CCA GTT TCC TTT TGG AGG ATT 2524 |
| Ala | Leu | Asp | Glu | Ser | Ile | Pro | Pro Val Ser Phe Trp Arg Ile |
| 2525 ATG | AAG | CTA | AAT | TTA | ACT | GAA | TGG CCT TAT TTT GTT GTT GGT 2566 |
| MET | Lys | Leu | Asn | Leu | Thr | Glu | Trp Pro Tyr Phe Val Val Gly |
| 2567 GTA | TTT | TGT | GCC | ATT | ATA | AAT | GGA GGC CTG CAA CCA GCA TTT 2608 |
| Val | Phe | Cys | Ala | Ile | Ile | Asn | Gly Gly Leu Gln Pro Ala Phe |
| 2609 GCA | ATA | ATA | TTT | TCA | AAG | ATT | ATA GGG GTT TTT ACA AGA ATT 2650 |
| Ala | Ile | Ile | Phe | Ser | Lys | Ile | Ile Gly Val Phe Thr Arg Ile |
| 2651 GAT | GAT | CCT | GAA | ACA | CGA | AAA | CAG AAT AGT TTG TTT TCA 2692 |
| Asp | Asp | Pro | Glu | Thr | Arg | Lys | Gln Asn Ser Leu Phe Ser |
| 2693 CTA | TTG | TTT | CTA | GCC | CTT | GGA | ATT ATT TCT TTT ATT ACA TTT 2734 |
| Leu | Leu | Phe | Leu | Ala | Leu | Gly | Ile Ile Ser Phe Ile Thr Phe |
| 2735 TTC | CTT | CAG | GGT | TTC | ACA | TTT | GGC AAA GCT GGA GAG ATC CTC 2776 |
| Phe | Leu | Gln | Gly | Phe | Thr | Phe | Gly Lys Ala Gly Glu Ile Leu |

FIG. 4G

| | | | | | | | | | |
|---|---|---|---|---|---|---|---|---|---|
| 2777 | ACC Thr | AAG Lys | CGG Arg | CTC Leu | CGA Arg | TAC Tyr | ATG MET | GTT Val | TTC Phe | CGA Arg | TCC Ser | AGG MET | CTC Leu | AGA Arg | 2818 |
| 2819 | CAG Gln | GAT Asp | GTG Val | AGT Ser | TGG Trp | TTT Phe | GAT Asp | ACT Thr | AAA Lys | AAC Asn | ACC Thr | AAT Thr | ACT Thr | GGA Gly | 2860 |
| 2861 | GCA Ala | TTG Leu | ACT Thr | AGG Arg | CTC Leu | GCC Ala | AAT Asn | GAT Asp | GCT Ala | CAA Gln | GCT Ala | CAA Gln | GTT Val | AAA Lys | 2902 |
| 2903 | GGG Gly | GCT Ala | ATA Ile | GGT Gly | TCC Ser | AGG Arg | CTT Leu | GCT Ala | GTA Val | ATT Ile | ACC Thr | CAG Gln | AAT Asn | ATA Ile | 2944 |
| 2945 | GCA Ala | AAT Asn | CTT Leu | GGG Gly | ACA Phr | GGA Gly | ATA Ile | ATT Ile | ATA Ile | TCC Ser | TTC Phe | ATC Ile | TAT Tyr | GGT Gly | 2986 |
| 2987 | TGG Trp | CAA Gln | CTA Leu | ACA Thr | CTG Leu | TTA Leu | CTC Leu | TTA Leu | GCA Ala | ATT Ile | GTA Val | CCC Pro | ATC Ile | ATT Ile | 3028 |
| 3029 | GCA Ala | GGA Gly | GTT Val | GTT Val | GAA Glu | ATG MET | AAA Lys | ATG MET | TTG Leu | TCT Ser | GGA Gly | CAA Gln | 3070 |
| 3071 | GCA Ala | CTG Leu | AAA Lys | GAT Asp | AAG Lys | GAA Glu | GAA Glu | CTA Leu | GAA Glu | GGT Gly | GCT Ala | GGG Gly | AAG Ays | ATC Ile | 3112 |
| 3113 | GCT Ala | GAA Glu | GCA Ala | ATA Ile | GAA Glu | AAC Asn | TTC Phe | CGA Arg | ACC Thr | GTT Val | TCT Ser | TTG Leu | 3154 |
| 3155 | ACT Thr | CAG Gln | GAG Glu | CAG Gln | AAG Lys | TTT Phe | GAA Glu | CAT His | ATG MET | TAT Tyr | GCT Ala | CAG Gln | AGT Ser | TTG Leu | 3196 |

FIG.4H

```
3197  CAG GTA CCA TAC AGA AAC TCT TTG AGG AAA GCA CAC ATC TTT  3238
      Gln Val Pro Tyr Arg Asn Ser Leu Arg Lys Ala His Ile Phe

3239  GGA ATT ACA TTT TCC TTC ACC CAG GCA ATG TAT TTT TCC       3280
      Gly Ile Thr Phe Ser Phe Thr Gln Ala MET Tyr Phe Ser

3281  TAT GCT GGA TGT TTC CGG TTT GGA GCC TAC TTG GTG GCA CAT   3322
      Tyr Ala Gly Cys Phe Arg Phe Gly Ala Tyr Leu Val Ala His

3323  AAA CTA ATG AGC TTT GAG GAT GTT CTG TTA GTA TTT TCA GCT   3364
      Lys Leu MET Ser Phe Glu Asp Val Leu Leu Val Phe Ser Ala

3365  GTT GTC TTT GGT GCC ATG GCC GTG GGG CAA GTC AGT TCA TTT   3406
      Val Val Phe Gly Ala MET Ala Val Gly Gln Val Ser Ser Phe

3407  GCT CCT GAC TAT GCC AAA ACC CCT TTG ATT GAC AGC TAC AGC   3448
      Ala Pro Asp Tyr Ala Lys Thr Pro Leu Ile Asp Ser Tyr Ser

3449  ATC ATG ATT GAA CTA ATG CCG AAC ACA TTG GAA GGA AAT GTC ACA  3490
      Ile MET Ile Glu Leu MET Pro Asn Thr Leu Glu Gly Asn Val Thr

3491  ACG GAA GGC CTA ATG CCG AAC ACA TTG GAA GGA AAT GTC ACA   3532
      Thr Glu Gly Leu MET Pro Asn Thr Leu Glu Gly Asn Val Thr

3533  TTT GGT GAA GTT GTA TTC AAC TAT CCC ACC CGA CCG GAC ATC   3574
      Phe Gly Glu Val Val Phe Asn Tyr Pro Thr Arg Pro Asp Ile

3575  CCA GTG CTT CAG GGA CTG AGC CTG GAG GTG AAG AAG GGC CAG   3616
      Pro Val Leu Gln Gly Leu Ser Leu Glu Val Lys Lys Gly Gln
```

FIG.4I

```
3617  ACG  CTG  GCT  CTG  GTG  GGC  AGC  AGT  GGC  TGT  GGG  AAG  AGC  ACA   3658
      Thr  Leu  Ala  Leu  Val  Gly  Ser  Ser  Gly  Cys  Gly  Lys  Ser  Thr

3659  GTG  GTC  CAG  CTC  CAG  CTG  GAG  CTG  TTC  TAC  GAC  CCC  TTG  GCA   3700
      Val  Val  Gln  Leu  Gln  Leu  Glu  Leu  Phe  Tyr  Asp  Pro  Leu  Ala   Gly
                                                                        GGG
                                                                        Gly

3701  AAA  GTG  CTG  CTT  GAT  GGC  AGT  ATA  AAG  CGA  CTG  CAG  AAT  GTT   3742
      Lys  Val  Leu  Leu  Asp  Gly  Ser  Ile  Lys  Arg  Leu  Gln  Asn  Val

3743  CAG  TGG  CTC  CGA  GCA  CAC  TTC  ATC  GTG  TCC  GAG  CCC         3784
      Gln  Trp  Leu  Arg  Ala  His  Phe  Ile  Val  Ser  Glu  Pro
                                     GGC                    CAG
                                     Gly                    Gln
                                                            CTG
                                                            Leu

3785  ATC  CTG  TTT  GAC  TGC  AGC  ATT  GCT  GAG  AAC  ATT  GCC  TAT  GGA   3826
      Ile  Leu  Phe  Asp  Cys  Ser  Ile  Ala  Glu  Asn  Ile  Ala  Tyr  Gly

3827  GAC  AAC  AGC  CGG  GTG  GTG  TCA  CAG  GAA  GAG  ATC  GTG  AGG  GCA   3868
      Asp  Asn  Ser  Arg  Val  Val  Ser  Gln  Glu  Glu  Ile  Val  Arg  Ala

3869  GCA  AAG  GAG  GCC  ATA  CAT  GCC  TTC  ATC  GAG  TCA  CTG  CCT   3910
      Ala  Lys  Glu  Ala  Ile  His  Ala  Phe  Ile  Glu  Ser  Leu  Pro
                                AAC                                                
                                Asn

3911  AAT  AAA  TAT  AGC  ACT  AAA  GTA  GGA  GAC  AAA  GGA  ACT  CAG  CTC   3952
      Asn  Lys  Tyr  Ser  Thr  Lys  Val  Gly  Asp  Lys  Gly  Thr  Gln  Leu

3953  TCT  GGT  GGC  CAG  CAA  CGC  ATT  GCC  ATA  GCT  CGT  GCC  CTT   3994
      Ser  Gly  Gly  Gln  Gln  Arg  Ile  Ala  Ile  Ala  Arg  Ala  Leu
                     AAA                                                      
                     Lys

3995  GTT  AGA  CAG  CCT  CAT  ATT  TTG  CTT  TTG  GAT  GAA  GCC  ACG  TCA   4036
      Val  Arg  Gln  Pro  His  Ile  Leu  Leu  Leu  Asp  Glu  Ala  Thr  Ser
```

FIG.4J

```
4037 GCT CTG GAT ACA GAA AGT GAA AAG GTT GTC CAA GAA GCC CTG    4078
     Ala Leu Asp Thr Glu Ser Glu Lys Val Val Gln Glu Ala Leu

4079 GAC AAA CCC AGA GAA GGC CGC ACC TGC ATT GTG ATT GCT CAC    4120
     Asp Lys Pro Arg Glu Gly Arg Thr Cys Ile Val Ile Ala His

4121 CGC CTG TCC ACC ATC CAG AAT GCA GAC TTA ATA GTG GTG TTT    4162
     Arg Leu Ser Thr Ile Gln Asn Ala Asp Leu Ile Val Val Phe

4163 CAG AAT GGC AGA GTC AAG GAG CAT GGC ACG CAT CAG CAG CTG    4204
     Gln Asn Gly Arg Val Lys Glu His Gly Thr His Gln Gln Leu

4205 CTG GCA CAG AAA GGC ATC TAT TTT TCA ATG GTC AGT GTC CAG    4246
     Leu Ala Gln Lys Gly Ile Tyr Phe Ser MET Val Ser Val Gln

4247 GCT GCA ACA AAG CGC CAG TGA                                4267
     Ala Gly Thr Lys Arg Gln TER

4268 ACTCTGACTG TATGAGATGT TAAATACTTT TTAATATTTG TTTAGATATG
4318 ACATTATTC  AAAGTTAAAA GCAAACACTT ACAGAATTAT GAAGAGGTAT
4368 CTGTTTAACA TTTCCTCACT CAACTTCAGA GTCTTCAGAG ACTTCGTAAT
4418 TAAAGGAACA GAGTGAGAGA CATCATCAAG TGGAGAGAAA TCATAGTTTA
4468 AACTGCATTA TAAATTTTAT AACAGAATTA AAGTAGATTT TAAAAGATAA
4518 AATGTGTAAT TTTGTTTATA TTTTCCCATT TGGACTGTAA CTGACTGCCT
4568 TGCTAAAAGA TTATAGAAGT AGCAAAAAGT ATTGAAATGT TTGCATAAAG
4618 TGTCTATAAT AAAACTAAAC TTTCATGTGA AAAAAAAAAA AAAAAAAAA
4668 AA
```

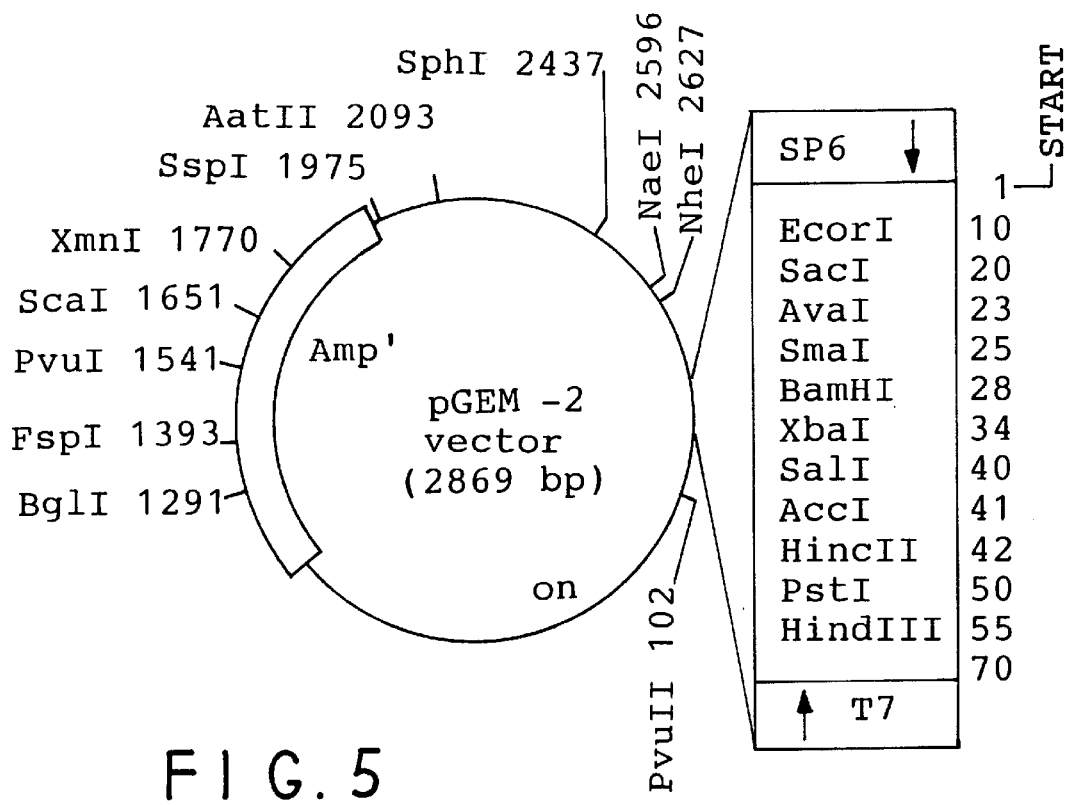
FIG. 5
FIG. 6
Restriction Map of pMDR 2000XS
(7.3 Kb)
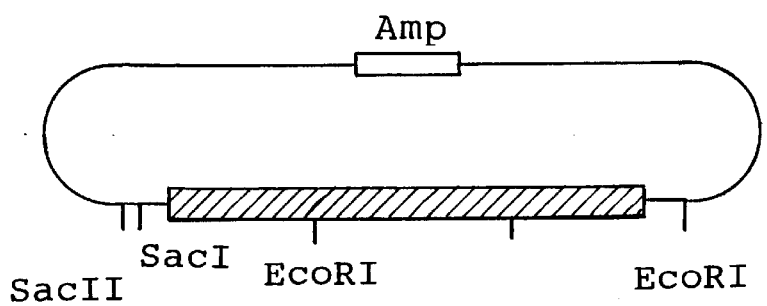

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 9 bases
        ( B ) TYPE: nucleic acid
        ( C ) STRANDEDNESS: singular
        ( D ) TOPOLOGY: linear ( i i ) MOLECULE TYPE:
        ( A ) DESCRIPTION: Genomic DNA ( x i ) SEQUENCE DESCRIPTION: SEQ ID NO:1:

C A G G T A T G C        9

( 2 ) INFORMATION FOR SEQ ID NO:2:

( i ) SEQUENCE CHARACTERISTICS:
        ( A ) LENGTH: 16 bases
        ( B ) TYPE: nucleic acid
        ( C ) STRANDEDNESS: singular
        ( D ) TOPOLOGY: linear ( i i ) MOLECULE TYPE:
        ( A ) DESCRIPTION: Genomic DNA ( x i ) SEQUENCE DESCRIPTION: SEQ ID NO:2:

ACATTTTTCC TTCAGG                                                                                        16

( 2 ) INFORMATION FOR SEQ ID NO:3:

( i ) SEQUENCE CHARACTERISTICS:
( A ) LENGTH: 50 bases
( B ) TYPE: nucleic acid
( C ) STRANDEDNESS: singular
( D ) TOPOLOGY: linear ( i i ) MOLECULE TYPE:
( A ) DESCRIPTION: Genomic DNA ( x i ) SEQUENCE DESCRIPTION: SEQ ID NO:3:

AGTGAACTCT GGTTAACTCC ACTCGAGCAC AGATCTGGAC ATCGATACTC                                                   50

( 2 ) INFORMATION FOR SEQ ID NO:4:

( i ) SEQUENCE CHARACTERISTICS:
( A ) LENGTH: 30 bases
( B ) TYPE: nucleic acid
( C ) STRANDEDNESS: singular
( D ) TOPOLOGY: linear ( i i ) MOLECULE TYPE:
( A ) DESCRIPTION: Genomic DNA ( x i ) SEQUENCE DESCRIPTION: SEQ ID NO:4:

TCTGTACTGG TCTATACGGA TAATAATGTC                                                                         30

( 2 ) INFORMATION FOR SEQ ID NO:5:

( i ) SEQUENCE CHARACTERISTICS:
( A ) LENGTH: 30 bases
( B ) TYPE: nucleic acid
( C ) STRANDEDNESS: singular
( D ) TOPOLOGY: linear ( i i ) MOLECULE TYPE:
( A ) DESCRIPTION: Genomic DNA ( x i ) SEQUENCE DESCRIPTION: SEQ ID NO:5:

CTAATTACTT CCATAACCAC TGTTTTAACC                                                                         30

( 2 ) INFORMATION FOR SEQ ID NO:6:

( i ) SEQUENCE CHARACTERISTICS:
( A ) LENGTH: 30 bases
( B ) TYPE: nucleic acid
( C ) STRANDEDNESS: singular
( D ) TOPOLOGY: linear ( i i ) MOLECULE TYPE:
( A ) DESCRIPTION: Genomic DNA ( x i ) SEQUENCE DESCRIPTION: SEQ ID NO:6:

GTAAAAAGGA AGTTCCAAAG TGTAAACCGT                                                                         30

( 2 ) INFORMATION FOR SEQ ID NO:7:

( i ) SEQUENCE CHARACTERISTICS:
( A ) LENGTH: 33 bases
( B ) TYPE: nucleic acid
( C ) STRANDEDNESS: singular
( D ) TOPOLOGY: linear ( i i ) MOLECULE TYPE:
( A ) DESCRIPTION: DNA primer ( x i ) SEQUENCE DESCRIPTION: SEQ ID NO:7:

GGAAGACATG ACCAGATATG CCTATTATTA CAG 33

( 2 ) INFORMATION FOR SEQ ID NO:8:

( i ) SEQUENCE CHARACTERISTICS:
( A ) LENGTH: 33 bases
( B ) TYPE: nucleic acid
( C ) STRANDEDNESS: singular
( D ) TOPOLOGY: linear ( i i ) MOLECULE TYPE:
( A ) DESCRIPTION: DNA primer ( x i ) SEQUENCE DESCRIPTION: SEQ ID NO:8:

CTGTAATAAT AGGCATATCT GGTCATGTCT TCC 33

( 2 ) INFORMATION FOR SEQ ID NO:9:

( i ) SEQUENCE CHARACTERISTICS:
( A ) LENGTH: 35 bases
( B ) TYPE: nucleic acid
( C ) STRANDEDNESS: singular
( D ) TOPOLOGY: linear ( i i ) MOLECULE TYPE:
( A ) DESCRIPTION: DNA primer ( x i ) SEQUENCE DESCRIPTION: SEQ ID NO:9:

CTCTAAGATT AATGAAGGTA TTGGTGACAA AATTG 35

( 2 ) INFORMATION FOR SEQ ID NO:10:

( i ) SEQUENCE CHARACTERISTICS:
( A ) LENGTH: 35 bases
( B ) TYPE: nucleic acid
( C ) STRANDEDNESS: singular
( D ) TOPOLOGY: linear ( i i ) MOLECULE TYPE:
( A ) DESCRIPTION: DNA primer ( x i ) SEQUENCE DESCRIPTION: SEQ ID NO:10:

CAATTTTGTC ACCAATACCT TCATTAATCT TAGAG 35

( 2 ) INFORMATION FOR SEQ ID NO:11:

( i ) SEQUENCE CHARACTERISTICS:
( A ) LENGTH: 31 bases
( B ) TYPE: nucleic acid
( C ) STRANDEDNESS: singular
( D ) TOPOLOGY: linear ( i i ) MOLECULE TYPE:
( A ) DESCRIPTION: DNA primer ( x i ) SEQUENCE DESCRIPTION: SEQ ID NO:11:

ATCGCGGATC CATGGTGGTG GGAACTTTGG C 31

( 2 ) INFORMATION FOR SEQ ID NO:12:

( i ) SEQUENCE CHARACTERISTICS:
( A ) LENGTH: 40 bases
( B ) TYPE: nucleic acid
( C ) STRANDEDNESS: singular
( D ) TOPOLOGY: linear ( i i ) MOLECULE TYPE:
( A ) DESCRIPTION: DNA primer ( x i ) SEQUENCE DESCRIPTION: SEQ ID NO:12:

CATCCGGAAT TCAGCTGACA GTCCAAGAAC AGGACTGATG     40

( 2 ) INFORMATION FOR SEQ ID NO:13:

( i ) SEQUENCE CHARACTERISTICS:
        ( A ) LENGTH: 58 bases
        ( B ) TYPE: nucleic acid
        ( C ) STRANDEDNESS: singular
        ( D ) TOPOLOGY: linear ( i i ) MOLECULE TYPE:
        ( A ) DESCRIPTION: DNA primer ( x i ) SEQUENCE DESCRIPTION: SEQ ID NO:13:

ATCGCGGATC CGGAATTATT TCTTTTATTA CATTTTCCT TCAAGGTTTC ACATTGG     58

( 2 ) INFORMATION FOR SEQ ID NO:14:

( i ) SEQUENCE CHARACTERISTICS:
        ( A ) LENGTH: 24 bases
        ( B ) TYPE: nucleic acid
        ( C ) STRANDEDNESS: singular
        ( D ) TOPOLOGY: linear ( i i ) MOLECULE TYPE:
        ( A ) DESCRIPTION: DNA primer ( x i ) SEQUENCE DESCRIPTION: SEQ ID NO:14:

CTCAAAGAGT TTCTGTATGG TACC     24

( 2 ) INFORMATION FOR SEQ ID NO:15:

( i ) SEQUENCE CHARACTERISTICS:
        ( A ) LENGTH: 18 bases
        ( B ) TYPE: nucleic acid
        ( C ) STRANDEDNESS: singular
        ( D ) TOPOLOGY: linear ( i i ) MOLECULE TYPE:
        ( A ) DESCRIPTION: DNA primer ( x i ) SEQUENCE DESCRIPTION: SEQ ID NO:15:

GCCCACATCA TCATGATC     18

( 2 ) INFORMATION FOR SEQ ID NO:16:

( i ) SEQUENCE CHARACTERISTICS:
        ( A ) LENGTH: 18 bases
        ( B ) TYPE: nucleic acid
        ( C ) STRANDEDNESS: singular
        ( D ) TOPOLOGY: linear ( i i ) MOLECULE TYPE:
        ( A ) DESCRIPTION: DNA primer ( x i ) SEQUENCE DESCRIPTION: SEQ ID NO:16:

GTCTCCTACT TTAGTGCT     18

( 2 ) INFORMATION FOR SEQ ID NO:17:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( i i ) MOLECULE TYPE:
        ( A ) DESCRIPTION: Plasmid DNA ( x i ) SEQUENCE DESCRIPTION: SEQ ID NO:17:

AATTCGCGGC CGCTACGTAG TCGACGGATC CCTCGAGAAG CTTGGGCCCA T    51

( 2 ) INFORMATION FOR SEQ ID NO:18:

( i ) SEQUENCE CHARACTERISTICS:
        ( A ) LENGTH: 4669 bases
        ( B ) TYPE: nucleic acid
        ( C ) STRANDEDNESS: singular
        ( D ) TOPOLOGY: linear ( i i ) MOLECULE TYPE:
        ( A ) DESCRIPTION: Genomic DNA ( x i ) SEQUENCE DESCRIPTION: SEQ ID NO:18:

| | | | | | |
|---|---|---|---|---|---|
| CCTACTCTAT | TCAGATATTC | TCCAGATTCC | TAAAGATTAG | AGATCATTTC | TCATTCTCCT | 60 |
| AGGAGTACTC | ACTTCAGGAA | GCAACCAGAT | AAAAGAGAGG | TGCAACGGAA | GCCAGAACAT | 120 |
| TCCTCCTGGA | AATTCAACCT | GTTTCGCAGT | TTCTCGAGGA | ATCAGCATTC | AGTCAATCCG | 180 |
| GGCCGGGACC | AGTCATCTGT | GGTGAGGCTG | ATTGGCTGGG | CAGGAACAGC | GCCGGGGCGT | 240 |
| GGGCTGAGCA | CAGCGCTTCG | CTCTCTTTGC | CACAGGAAGC | CTGAGCTCAT | TCGAGTAGCG | 300 |
| GCTCTTCCAA | GCTCAAAGAA | GCAGAGGCCG | CTGTTCGTTT | CCTTTAGGTC | TTTCCACTAA | 360 |
| AGTCGGAGTA | TCTTCTTCCA | AGATTTCACG | TCTTGGTGGC | CGTTCCAAGG | AGCGCGAGGT | 420 |
| CGGGATGGAT | CTTGAAGGGG | ACCGCAATGG | AGGAGCAAAG | AAGAAGAACT | TTTTTAAACT | 480 |
| GAACAATAAA | AGTGAAAAAG | ATAAGAAGGA | AAAGAAACCA | ACTGTCAGTG | TATTTTCAAT | 540 |
| GTTTCGCTAT | TCAAATTGGC | TTGACAAGTT | GTATATGGTG | GTGGGAACTT | GGCTGCCAT | 600 |
| CATCCATGGG | GCTGGACTTC | CTCTCATGAT | GCTGGTGTTT | GGAGAAATGA | CAGATATCTT | 660 |
| TGCAAATGCA | GGAAATTTAG | AAGATCTGAT | GTCAAACATC | ACTAATAGAA | GTGATATCAA | 720 |
| TGATACAGGG | TTCTTCATGA | ATCTGGAGGA | AGACATGACC | AGGTATGCCT | ATTATTACAG | 780 |
| TGGAATTGGT | GCTGGGGTGC | TGGTTGCTGC | TTACATTCAG | GTTTCATTTT | GGTGCCTGGC | 840 |
| AGCTGGAAGA | CAAATACACA | AAATTAGAAA | ACAGTTTTTT | CATGCTATAA | TGCGACAGGA | 900 |
| GATAGGCTGG | TTTGATGTGC | ACGATGTTGG | GCAGCTTAAC | ACCCGACTTA | CAGATGATGT | 960 |
| CTCTAAGATT | AATGAACTTA | TTGGTGACAA | AATTGGAATG | TTCTTTCAGT | CAATGGCAAC | 1020 |
| ATTTTTCACT | GGGTTTATAG | TAGGATTTAC | ACGTGGTTGG | AAGCTAACCC | TTGTGATTTT | 1080 |
| GGCCATCAGT | CCTGTTCTTG | GACTGTCAGC | TGCTGTCTGG | GCAAAGATAC | TATCTTCATT | 1140 |
| TACTGATAAA | GAACTCTTAG | CGTATGCAAA | AGCTGGAGCA | GTAGCTGAAG | AGGTCTTGGC | 1200 |
| AGCAATTAGA | ACTGTGATTG | CATTTGGAGG | ACAAAGAAA | GAACTTGAAA | GGTACAACAA | 1260 |
| AAATTTAGAA | GAAGCTAAAA | GAATTGGGAT | AAAGAAAGCT | ATTACAGCCA | ATATTTCTAT | 1320 |
| AGGTGCTGCT | TTCCTGCTGA | TCTATGCATC | TTATGCTCTG | GCCTTCTGGT | ATGGGACCAC | 1380 |
| CTTGGTCCTC | TCAGGGGAAT | ATTCTATTGG | ACAAGTACTC | ACTGTATTCT | TTTCTGTATT | 1440 |
| AATTGGGGCT | TTTAGTGTTG | GACAGGCATC | TCCAAGCATT | GAAGCATTTG | CAAATGCAAG | 1500 |
| AGGAGCAGCT | TATGAAATCT | TCAAGATAAT | TGATAATAAG | CCAAGTATTG | ACAGCTATTC | 1560 |
| GAAGAGTGGG | CACAAACCAG | ATAATATTAA | GGGAAATTTG | GAATTCAGAA | ATGTTCACTT | 1620 |
| CAGTTACCCA | TCTCGAAAAG | AAGTTAAGAT | CTTGAAGGGC | CTGAACCTGA | AGGTGCAGAG | 1680 |
| TGGGCAGACG | GTCCCCCTGG | TTGGAAACAG | TGGCTGTGGG | AAGAGCACAA | CAGTCCAGCT | 1740 |
| GATGCAGAGG | CTCTATGACC | CCACAGAGGG | GATGGTCAGT | GTTCATGGAC | AGGATATTAG | 1800 |
| GACCATAAAT | GTAAGGTTTC | TACGGGAAAT | CATTGGTGTG | GTGAGTCAGG | AACCTGTATT | 1860 |

| | | | | | |
|---|---|---|---|---|---|
| GTTTGCCACC | ACGATAGCTG | AAAACATTCG | CTATGGCCGT | GAAAATGTCA | CCATGGATGA | 1920
| GATTGAGAAA | GCTGTCAAGG | AAGCCAATGC | CTATGACTTT | ATCATGAAAC | TGCCTCATAA | 1980
| ATTTGACACC | CTGGTTGGAG | AGAGAGGGCC | CCAGTTGAGT | GGTGGGCAGA | AGCAGAGGAT | 2040
| CGCCATTGCA | CGTGCCCTGG | TTCGCAACCC | CAAGATCCTC | CTGCTGGATG | AGGCCACGTC | 2100
| AGCCTTGGAC | ACAGAAAGCG | AAGCAGTGGT | TCAGGTGGCT | CTGGATAAGG | CCAGAAAAGG | 2160
| TCGGACCACC | ATTGTGATAG | CTCATCGTTT | GTCTACAGTT | CGTAATGCTG | ACGTCATCGC | 2220
| TGGTTTCGAT | GATGGAGTCA | TTGTGGAGAA | AGGAAATCAT | GATGAACTCA | TGAAAGAGAA | 2280
| AGGCATTTAC | TTCAAACTTG | TCACAATGCA | GACAGCAGGA | AATGAAGTTG | AATTAGAAAA | 2340
| TGCAGCTGAT | GAATCCAAAA | GTGAAATTGA | TGCCTTGGAA | ATGTCTTCAA | ATGATTCAAG | 2400
| ATCACGTCTA | ATAAGAAAAA | GATCAACTCG | TAGGAGTGTC | CGTGGATCAC | AACCCCAAGA | 2460
| CAGAAAGCTT | AGTACCAAAG | AGGCTCTGGA | TGAAAGTATA | CCTCCAGTTT | CCTTTTGGAG | 2520
| GATTATGAAG | CTAAATTTAA | CTGAATGGCC | TTATTTTGTT | GTTGGTGTAT | TTGTGCCAT | 2580
| TATAAATGGA | GGCCTGCAAC | CAGCATTTGC | AATAATATTT | TCAAAGATTA | TAGGGGTTTT | 2640
| TACAAGAATT | GATGATCCTG | AAACAAAACG | ACAGAATACT | AACTTGTTTT | CACTATTGTT | 2700
| TCTAGCCCTT | GGAATTATTT | CTTTTATTAC | ATTTTTCCTT | CAGGGTTTCA | CATTTGGCAA | 2760
| AGCTGGAGAG | ATCCTCACCA | AGCGGCTCCG | ATACATGGTT | TTCCGATCCA | TGCTCAGACA | 2820
| GGATGTGAGT | TGGTTTGATG | ACCCTAAAAA | CACCACTGGA | GCATTGACTA | CCAGGCTCGC | 2880
| CAATGATGCT | GCTCAAGTTA | AAGGGGCTAT | AGGTTCCAGG | CTTGCTGTAA | TTACCCAGAA | 2940
| TATAGCAATT | CTTGGGACAG | GAATAATTAT | ATCCTTCATC | TATGGTTGGC | AACTAACACT | 3000
| GTTACTCTTA | GCAATTGTAC | CCATCATTGC | AATAGCAGGA | GTTGTTGAAA | TGAAAATGTT | 3060
| GTCTGGACAA | GCACTGAAAG | ATAAGAAAGA | ACTAGAAGGT | GCTGGGAAGA | TCGCTACTGA | 3120
| AGCAATAGAA | AACTTCCGAA | CCGTTGTTTC | TTTGACTCAG | GAGCAGAAGT | TGAACATAT | 3180
| GTATGCTCAG | AGTTTGCAGG | TACCATACAG | AAACTCTTTG | AGGAAAGCAC | ACATCTTTGG | 3240
| AATTACATTT | TCCTTCACCC | AGGCAATGAT | GTATTTTTCC | TATGCTGGAT | GTTTCCGGTT | 3300
| TGGAGCCTAC | TTGGTGGCAC | ATAAACTAAT | GAGCTTTGAG | GATGTTCTGT | TAGTATTTTC | 3360
| AGCTGTTGTC | TTTGGTGCCA | TGGCCGTGGG | GCAAGTGAGT | TCATTTGCTC | CTGACTATGC | 3420
| CAAAGCCAAA | ATATCAGCAG | CCCACATCAT | CATGATCATT | GAAAAAACCC | CTTTGATTGA | 3480
| CAGCTACAGC | ACGGAAGGCC | TAATGCCGAA | CACATTGGAA | GGAAATGTCA | CATTTGGTGA | 3540
| AGTTGTATTC | AACTATCCCA | CCCGACCGGA | CATCCCAGTC | CTTCAGGGAC | TGAGCCTGGA | 3600
| GGTGAAGAAG | GGCCAGACGC | TGGCTCTGGT | GGGCAGCAGT | GGCTGTGGGA | AGAGCACAGT | 3660
| GGTCCAGCTC | CTGGAGCGGT | TCTACGACCC | CTTGGCAGGG | AAAGTGCTGC | TTGATGGCAA | 3720
| AGAAATAAAG | CGACTGAATG | TTCAGTGGCT | CCGAGCACAC | CTGGGCATCG | TGTCCCAGGA | 3780
| GCCCATCCTG | TTTGACTGCA | GCATTGCTGA | GAACATTGCC | TATGGACACA | ACAGCGGGT | 3840
| GGTGTCACAG | GAAGAGATCG | TGAGGGCAGC | AAAGGAGGCC | AACATACATG | CCTTCATCGA | 3900
| GTCACTGCCT | AATAAATATA | GCACTAAAGT | AGGAGACAAA | GGAACTCAGC | TCTCTGGTGG | 3960
| CCAGAAACAA | CGCATTGCCA | TAGCTCGTGC | CCTTGTTAGA | CAGCCTCATA | TTTTGCTTTT | 4020
| GGATGAAGCC | ACGTCAGCTC | TGGATACAGA | AAGTGAAAAG | GTTGTCCAAG | AAGCCCTGGA | 4080
| CAAACCCAGA | GAAGGCCGCA | CCTGCATTGT | GATTGCTCAC | CGCCTGTCCA | CCATCCAGAA | 4140
| TGCAGACTTA | ATAGTGGTGT | TTCAGAATGG | CAGAGTCAAG | CAGCATGGCA | CGCATCAGCA | 4200
| GCTGCTGGCA | CAGAAAGGCA | TCTATTTTTC | AATGGTCAGT | GTCCAGCCTG | GAACAAAGCG | 4260

```
CCAGTGAACT  CTGACTGTAT  GAGATGTTAA  ATACTTTTTA  ATATTTGTTT  AGATATGACA      4320

TTTATTCAAA  GTTAAAAGCA  AACACTTACA  GAATTATGAA  GAGGTATCTG  TTTAACATTT      4380

CCTCACTCAA  CTTCAGAGTC  TTCAGAGACT  TCGTAATTAA  AGGAACAGAG  TGAGAGACAT      4440

CATCAAGTGG  AGAGAAATCA  TAGTTTAAAC  TGCATTATAA  ATTTTATAAC  AGAATTAAAG      4500

TAGATTTTAA  AAGATAAAAT  GTGTAATTTT  GTTTATATTT  TCCCATTTGG  ACTGTAACTG      4560

ACTGCCTTGC  TAAAAGATTA  TAGAAGTAGC  AAAAAGTATT  GAAATGTTTG  CATAAAGTGT      4620

CTATAATAAA  ACTAAACTTT  CATGTGAAAA  AAAAAAAAA   AAAAAAAA                    4669
```

(2) INFORMATION FOR SEQ ID NO:19:

( i ) SEQUENCE CHARACTERISTICS:
        ( A ) LENGTH: 1280 amino acids
        ( B ) TYPE: amino acid
        ( C ) STRANDEDNESS:
        ( D ) TOPOLOGY: linear ( i i ) MOLECULE TYPE:
        ( A ) DESCRIPTION: protein ( x i ) SEQUENCE DESCRIPTION: SEQ ID NO:19:

```
Met  Asp  Leu  Glu  Gly  Asp  Arg  Asn  Gly  Gly  Ala  Lys  Lys  Lys  Asn
               5                        10                           15

Phe  Phe  Lys  Leu  Asn  Asn  Lys  Ser  Glu  Lys  Asp  Lys  Lys  Glu  Lys
              20                        25                           30

Lys  Pro  Thr  Val  Ser  Val  Phe  Ser  Met  Phe  Arg  Tyr  Ser  Asn  Trp
              35                        40                           45

Leu  Asp  Lys  Leu  Tyr  Met  Val  Val  Gly  Thr  Leu  Ala  Ala  Ile  Ile
              50                        55                           60

His  Gly  Ala  Gly  Leu  Pro  Leu  Met  Met  Leu  Val  Phe  Gly  Glu  Met
              65                        70                           75

Thr  Asp  Ile  Phe  Ala  Asn  Ala  Gly  Asn  Leu  Glu  Asp  Leu  Met  Ser
              80                        85                           90

Asn  Ile  Thr  Asn  Arg  Ser  Asp  Ile  Asn  Asp  Thr  Gly  Phe  Phe  Met
              95                       100                          105

Asn  Leu  Glu  Glu  Asp  Met  Thr  Arg  Tyr  Ala  Tyr  Tyr  Tyr  Ser  Gly
             110                       115                          120

Ile  Gly  Ala  Gly  Val  Leu  Val  Ala  Ala  Tyr  Ile  Gln  Val  Ser  Phe
             125                       130                          135

Trp  Cys  Leu  Ala  Ala  Gly  Arg  Gln  Ile  His  Lys  Ile  Arg  Lys  Gln
             140                       145                          150

Phe  Phe  His  Ala  Ile  Met  Arg  Gln  Glu  Ile  Gly  Trp  Phe  Asp  Val
             155                       160                          165

His  Asp  Val  Gly  Glu  Leu  Asn  Thr  Arg  Leu  Thr  Asp  Asp  Val  Ser
             170                       175                          180

Lys  Ile  Asn  Glu  Val  Ile  Gly  Asp  Lys  Ile  Gly  Met  Phe  Phe  Gln
             185                       190                          195

Ser  Met  Ala  Thr  Phe  Phe  Thr  Gly  Phe  Ile  Val  Gly  Phe  Thr  Arg
             200                       205                          210

Gly  Trp  Lys  Leu  Thr  Leu  Val  Ile  Leu  Ala  Ile  Ser  Pro  Val  Leu
             215                       220                          225

Gly  Leu  Ser  Ala  Ala  Val  Trp  Ala  Lys  Ile  Leu  Ser  Ser  Phe  Thr
             230                       235                          240

Asp  Lys  Glu  Leu  Leu  Ala  Tyr  Ala  Lys  Ala  Gly  Ala  Val  Ala  Glu
             245                       250                          255
```

| | | | | | | | | | | | | | |
|---|---|---|---|---|---|---|---|---|---|---|---|---|---|
| Glu | Val | Leu | Ala | Ala 260 | Ile | Arg | Thr | Val 265 | Ile | Ala | Phe | Gly | Gly | Gln 270 |
| Lys | Lys | Glu | Leu | Glu 275 | Arg | Tyr | Asn | Lys 280 | Asn | Leu | Glu | Glu | Ala | Lys 285 |
| Arg | Ile | Gly | Ile | Lys 290 | Lys | Ala | Ile | Thr 295 | Ala | Asn | Ile | Ser | Ile | Gly 300 |
| Ala | Ala | Phe | Leu | Leu 305 | Ile | Tyr | Ala | Ser 310 | Tyr | Ala | Leu | Ala | Phe | Trp 315 |
| Tyr | Gly | Thr | Thr | Leu 320 | Val | Leu | Ser | Gly 325 | Glu | Tyr | Ser | Ile | Gly | Gln 330 |
| Val | Leu | Thr | Val | Phe 335 | Phe | Ser | Val | Leu 340 | Ile | Gly | Ala | Phe | Ser | Val 345 |
| Gly | Gln | Ala | Ser | Pro 350 | Ser | Ile | Glu | Ala 355 | Phe | Ala | Asn | Ala | Arg | Gly 360 |
| Ala | Ala | Tyr | Glu | Ile 365 | Phe | Lys | Ile | Ile 370 | Asp | Asn | Lys | Pro | Ser | Ile 375 |
| Asp | Ser | Tyr | Ser | Lys 380 | Ser | Gly | His | Lys 385 | Pro | Asp | Asn | Ile | Lys | Gly 390 |
| Asn | Leu | Glu | Phe | Arg 395 | Asn | Val | His | Phe 400 | Ser | Tyr | Pro | Ser | Arg | Lys 405 |
| Glu | Val | Lys | Ile | Leu 410 | Lys | Gly | Leu | Asn 415 | Leu | Lys | Val | Gln | Ser | Gly 420 |
| Gln | Thr | Val | Ala | Leu 425 | Val | Gly | Asn | Ser 430 | Gly | Cys | Gly | Lys | Ser | Thr 435 |
| Thr | Val | Gln | Leu | Met 440 | Gln | Arg | Leu | Tyr 445 | Asp | Pro | Thr | Glu | Gly | Met 450 |
| Val | Ser | Val | Asp | Gly 455 | Gln | Asp | Ile | Arg 460 | Thr | Ile | Asn | Val | Arg | Phe 465 |
| Leu | Arg | Glu | Ile | Ile 470 | Gly | Val | Val | Ser 475 | Gln | Glu | Pro | Val | Leu | Phe 480 |
| Ala | Thr | Thr | Ile | Ala 485 | Glu | Asn | Ile | Arg 490 | Tyr | Gly | Arg | Gln | Asn | Val 495 |
| Thr | Met | Asp | Glu | Ile 500 | Glu | Lys | Ala | Val 505 | Lys | Glu | Ala | Asn | Ala | Tyr 510 |
| Asp | Phe | Ile | Met | Lys 515 | Leu | Pro | His | Lys 520 | Phe | Asp | Thr | Leu | Val | Gly 525 |
| Glu | Arg | Gly | Ala | Gln 530 | Leu | Ser | Gly | Gly 535 | Gln | Lys | Gln | Arg | Ile | Ala 540 |
| Ile | Ala | Arg | Ala | Leu 545 | Val | Arg | Asn | Pro 550 | Lys | Ile | Leu | Leu | Leu | Asp 555 |
| Glu | Ala | Thr | Ser | Ala 560 | Leu | Asp | Thr | Glu 565 | Ser | Glu | Ala | Val | Val | Gln 570 |
| Val | Ala | Leu | Asp | Lys 575 | Ala | Arg | Lys | Gly 580 | Arg | Thr | Thr | Ile | Val | Ile 585 |
| Ala | His | Arg | Leu | Ser 590 | Thr | Val | Arg | Asn 595 | Ala | Asp | Val | Ile | Ala | Gly 600 |
| Phe | Asp | Asp | Gly | Val 605 | Ile | Val | Glu | Lys 610 | Gly | Asn | His | Asp | Glu | Leu 615 |
| Met | Lys | Glu | Lys | Gly 620 | Ile | Tyr | Phe | Lys 625 | Leu | Val | Thr | Met | Gln | Thr 630 |
| Ala | Gly | Asn | Glu | Val 635 | Glu | Leu | Glu | Asn 640 | Ala | Ala | Asp | Glu | Ser | Lys 645 |
| Ser | Glu | Ile | Asp | Ala 650 | Leu | Glu | Met | Ser 655 | Ser | Asn | Asp | Ser | Arg | Ser 660 |

```
Ser Leu Ile Arg Lys Arg Ser Thr Arg Arg Ser Val Arg Gly Ser
                665                 670                 675
Gln Ala Gln Asp Arg Lys Leu Ser Thr Lys Glu Ala Leu Asp Glu
                680                 685                 690
Ser Ile Pro Pro Val Ser Phe Trp Arg Ile Met Lys Leu Asn Leu
                695                 700                 705
Thr Glu Trp Pro Tyr Phe Val Val Gly Val Phe Cys Ala Ile Ile
                710                 715                 720
Asn Gly Gly Leu Gln Pro Ala Phe Ala Ile Ile Phe Ser Lys Ile
                725                 730                 735
Ile Gly Val Phe Thr Arg Ile Asp Asp Pro Glu Thr Lys Arg Gln
                740                 745                 750
Asn Ser Asn Leu Phe Ser Leu Leu Phe Leu Ala Leu Gly Ile Ile
                755                 760                 765
Ser Phe Ile Thr Phe Phe Leu Gln Gly Phe Thr Phe Gly Lys Ala
                770                 775                 780
Gly Glu Ile Leu Thr Lys Arg Leu Arg Tyr Met Val Phe Arg Ser
                785                 790                 795
Met Leu Arg Gln Asp Val Ser Trp Phe Asp Asp Pro Lys Asn Thr
                800                 805                 810
Thr Gly Ala Leu Thr Thr Arg Leu Ala Asn Asp Ala Ala Gln Val
                815                 820                 825
Lys Gly Ala Ile Gly Ser Arg Leu Ala Val Ile Thr Gln Asn Ile
                830                 835                 840
Ala Asn Leu Gly Thr Gly Ile Ile Ile Ser Phe Ile Tyr Gly Trp
                845                 850                 855
Gln Leu Thr Leu Leu Leu Leu Ala Ile Val Pro Ile Ile Ala Ile
                860                 865                 870
Ala Gly Val Val Glu Met Lys Met Leu Ser Gly Gln Ala Leu Lys
                875                 880                 885
Asp Lys Lys Glu Leu Glu Gly Ala Gly Lys Ile Ala Thr Glu Ala
                890                 895                 900
Ile Glu Asn Phe Arg Thr Val Val Ser Leu Thr Gln Glu Gln Lys
                905                 910                 915
Phe Glu His Met Tyr Ala Gln Ser Leu Gln Val Pro Tyr Arg Asn
                920                 925                 930
Ser Leu Arg Lys Ala His Ile Phe Gly Ile Thr Phe Ser Phe Thr
                935                 940                 945
Gln Ala Met Met Tyr Phe Ser Tyr Ala Gly Cys Phe Arg Phe Gly
                950                 955                 960
Ala Tyr Leu Val Ala His Lys Leu Met Ser Phe Glu Asp Val Leu
                965                 970                 975
Leu Val Phe Ser Ala Val Val Phe Gly Ala Met Ala Val Gly Gln
                980                 985                 990
Val Ser Ser Phe Ala Pro Asp Tyr Ala Lys Ala Lys Ile Ser Ala
                995                 1000                1005
Ala His Ile Ile Met Ile Ile Glu Lys Thr Pro Leu Ile Asp Ser
                1010                1015                1020
Tyr Ser Thr Glu Gly Leu Met Pro Asn Thr Leu Glu Gly Asn Val
                1025                1030                1035
Thr Phe Gly Glu Val Val Phe Asn Tyr Pro Thr Arg Pro Asp Ile
                1040                1045                1050
Pro Val Leu Gln Gly Leu Ser Leu Glu Val Lys Lys Gly Gln Thr
```

-continued

|  |  |  |  |  |  |  |  |  |  |  |  |  |  |  |
|---|---|---|---|---|---|---|---|---|---|---|---|---|---|---|
|  |  |  |  | 1055 |  |  |  | 1060 |  |  |  | 1065 |  |  |
| Leu | Ala | Leu | Val | Gly | Ser | Ser | Gly | Cys | Gly | Lys | Ser | Thr | Val | Val |
|  |  |  |  | 1070 |  |  |  | 1075 |  |  |  | 1080 |  |  |
| Gln | Leu | Leu | Glu | Arg | Phe | Tyr | Asp | Pro | Leu | Ala | Gly | Lys | Val | Leu |
|  |  |  |  | 1085 |  |  |  | 1090 |  |  |  | 1095 |  |  |
| Leu | Asp | Gly | Lys | Glu | Ile | Lys | Arg | Leu | Asn | Val | Gln | Trp | Leu | Arg |
|  |  |  |  | 1100 |  |  |  | 1105 |  |  |  | 1110 |  |  |
| Ala | His | Leu | Gly | Ile | Val | Ser | Gln | Glu | Pro | Ile | Leu | Phe | Asp | Cys |
|  |  |  |  | 1115 |  |  |  | 1120 |  |  |  | 1125 |  |  |
| Ser | Ile | Ala | Glu | Asn | Ile | Ala | Tyr | Gly | Asp | Asn | Ser | Arg | Val | Val |
|  |  |  |  | 1130 |  |  |  | 1135 |  |  |  | 1140 |  |  |
| Ser | Gln | Glu | Glu | Ile | Val | Arg | Ala | Ala | Lys | Glu | Ala | Asn | Ile | His |
|  |  |  |  | 1145 |  |  |  | 1150 |  |  |  | 1155 |  |  |
| Ala | Phe | Ile | Glu | Ser | Leu | Pro | Asn | Lys | Tyr | Ser | Thr | Lys | Val | Gly |
|  |  |  |  | 1160 |  |  |  | 1165 |  |  |  | 1170 |  |  |
| Asp | Lys | Gly | Thr | Gln | Leu | Ser | Gly | Gly | Gln | Lys | Gln | Arg | Ile | Ala |
|  |  |  |  | 1175 |  |  |  | 1180 |  |  |  | 1185 |  |  |
| Ile | Ala | Arg | Ala | Leu | Val | Arg | Gln | Pro | His | Ile | Leu | Leu | Leu | Asp |
|  |  |  |  | 1190 |  |  |  | 1195 |  |  |  | 1200 |  |  |
| Glu | Ala | Thr | Ser | Ala | Leu | Asp | Thr | Glu | Ser | Glu | Lys | Val | Val | Gln |
|  |  |  |  | 1205 |  |  |  | 1210 |  |  |  | 1215 |  |  |
| Glu | Ala | Leu | Asp | Lys | Ala | Arg | Glu | Gly | Arg | Thr | Cys | Ile | Val | Ile |
|  |  |  |  | 1220 |  |  |  | 1225 |  |  |  | 1230 |  |  |
| Ala | His | Arg | Leu | Ser | Thr | Ile | Gln | Asn | Ala | Asp | Leu | Ile | Val | Val |
|  |  |  |  | 1235 |  |  |  | 1240 |  |  |  | 1245 |  |  |
| Phe | Gln | Asn | Gly | Arg | Val | Lys | Glu | His | Gly | Thr | His | Gln | Gln | Leu |
|  |  |  |  | 1250 |  |  |  | 1255 |  |  |  | 1260 |  |  |
| Leu | Ala | Gln | Lys | Gly | Ile | Tyr | Phe | Ser | Met | Val | Ser | Val | Gln | Ala |
|  |  |  |  | 1265 |  |  |  | 1270 |  |  |  | 1275 |  |  |
| Gly | Thr | Lys | Arg | Gln |  |  |  |  |  |  |  |  |  |  |
|  |  |  |  | 1280 |  |  |  |  |  |  |  |  |  |  |

EXPRESSION OF HUMAN MULTIDRUG RESISTANCE GENES AND IMPROVED SELECTION OF CELLS TRANSDUCED WITH SUCH GENES

This application is a continuation of application Ser. No. 08/032,444, filed Oct. 31, 1994, now abandoned, which is a continuation of application Ser. No. 07/887,712 filed May 22, 1992, now abandoned.

This invention relates to the transduction of cells with human multidrug resistance (mdr) genes and the expression thereof, as well as the selection or identification of cells transduced with such genes. More particularly, this invention relates to the enhanced expression of mdr genes by transduced cells, and an improved method of selecting or identifying cells transduced with mdr genes.

Genes for multidrug resistance such as, for example, mdr1 and mutated forms thereof, encode proteins of a class known as p-glycoprotein, that confer resistance to a range of cytotoxic drugs used in the treatment of human malignancies. The introduction and expression of the mdr1 gene in human cells may serve several useful purposes in the treatment of diseases. For example, the mdr1 gene can function as a dominant selectable marker that will allow for positive selection of cells transduced by an expression vehicle, such as, for example, a retroviral vector, ex vivo or in vivo. Used in this manner, expression of the mdr1 gene in normal human cells may be useful in increasing the proportion of a target cell population that has been transformed by an expression vehicle, such as a retroviral particle. Also, expression of the mdr1 gene in normal human cells may permit more intensive use of chemotherapeutic drugs in the treatment of cancer. For example, expression of the mdr1 gene in human bone marrow cells could reduce the severity and duration of cytopenias following chemotherapy, which may facilitate dose intensification while reducing morbidity and mortality.

In accordance with an aspect of the present invention, there is provided human mdr1 DNA or RNA which encodes p-glycoprotein or an analogue or fragment of such DNA or RNA which encodes an iso-form of p-glycoprotein which confers multidrug resistance. The DNA or RNA includes at least one splice site, and at least one base in the splice site has been changed to a different base which thereby inactivates the splice site. Preferably, the DNA or RNA is a DNA or RNA sequence for human mdr1 which encodes p-glycoprotein wherein at least one base in a splice site of said DNA encoding p-glycoprotein is changed.

The natural human mdr1 gene contains at least one functional splice donor site and splice acceptor site. This invention provides a modification of the mdr1 gene whereby at least one base in a splice site has been changed to a different base which thereby inactivates the splice site.

The term "human mdr1 gene" as used herein means the wild type human mdr1 gene, which encodes p-glycoprotein, as well as mutated human mdr1 genes which encode what are known as iso-forms of p-glycoprotein. Such mutated genes include a mutation in which the human mdr1 DNA encodes a p-glycoprotein in which the first 23 pk amino acids at the N-terminal are deleted (Currier, et al., *J. Biol. Chem.,* Vol. 264, pgs. 14376–14381 (1989)); insertional mutation(s) in the human mdr1 DNA in which amino acids have been inserted into ATP binding or utilization sites (Currier, et al; 1989); a complementary human mdr1 DNA sequence (cDNA sequence) in which codon 185, which encodes Gly 185, has been changed from GGT to GTT to encode Val 185. (PCT Application No. W087/05943; Choi, et al., *Cell,* Vol. 53, pgs. 519–529 (1988); Safa, et al., *Proc.Nat.Acad.Sci.,* Vol. 87, pgs. 7225–7229 (1990)); and a chimeric gene encoding a protein having adenosine deaminase added to the N-terminal of p-glycoprotein (Germann, et al., *J. Biol. Chem.,* Vol. 264, pgs. 7418–7424 (1989)).

Although the scope of this aspect of the present invention is not to be limited to any theoretical reasoning, Applicants have found that aberrant splicing of the mdr1 gene may occur within the coding sequence for p-glycoprotein. Such splicing, which uses cryptic splice donor and splice acceptor sites, results in the production of expression vehicles (such as, for example, recombinant retroviruses) that contain a truncated mdr1 gene, which encodes a truncated and non-functional p-glycoprotein.

Applicants have found a cryptic splice donor site having a length of 9 bases from nucleotide 760 to nucleotide 768 of the human mdr1 gene, and which has the following sequence:
CAGGTATGC (SEQ ID NO:1)
A cryptic splice acceptor site was also found, which has a length of 16 bases from nucleotide 2729 to nucleotide 2744 of the human mdr1 gene; and which has the following sequence:
ACATTTTTCCTTCAGG (SEQ ID NO:2)
Applicants have found that, by changing at least one base of the cryptic splice donor and/or acceptor sites, one may suppress aberrant splicing of the mdr1 gene and maximize the transfer of DNA encoding functional p-glycoprotein into desired cells.

In one embodiment, at least one base which is changed is in a splice donor site. In another embodiment, the at least one base which is changed is in a splice acceptor site. In yet another embodiment, at least one base is changed in a splice donor site and at least one base is changed in a splice acceptor site.

In a preferred embodiment, at least one base in a splice site which is changed is in the splice donor site and is at least one of guanine (G) or thymine (T) contained in the splice donor site wherein G and T are adjacent.

In another preferred embodiment, at least one base in a splice site which is changed is in the splice acceptor site and is at least one of adenine (A) or guanine (G) contained in the splice acceptor site wherein A and G are adjacent.

In a more preferred embodiment, at least one base is changed in the splice donor site wherein the at least one base is at least one of G or T contained in the splice donor site wherein G and T are adjacent; and at least one base is changed in the splice acceptor site wherein the at least one base is at least one of A or G contained in the splice acceptor site wherein A and G are adjacent.

In another embodiment, at least one base in a splice site is changed such that a codon encoding an amino acid is changed to a different codon encoding the same amino acid. Preferably, the at least one base is the third, or "wobble" base in the codon.

In one embodiment, codon 113, located in the splice donor site, and which encodes Arg, is changed from AGG to AGA, which also encodes Arg. In another embodiment, codon 773, located in the splice acceptor site, and which encodes Gln, is changed from CAG to CAA, which also encodes Gln. It is also contemplated that in yet another embodiment, both codon 113 of the mdr1 gene is changed from AGG to AGA, and codon 773 of the mdr1 gene is changed from CAG to CAA.

In one embodiment, the DNA sequence is further mutated such that at least a portion of the 5' untranslated region of the DNA has been removed.

In another embodiment, the DNA sequence may be further mutated such that at least a portion of the 3' untranslated region of the DNA has been removed. In yet another embodiment, the DNA sequence is further mutated such that at least a portion of the 5' untranslated region of the DNA and at least a portion of the 3' untranslated region of the DNA have been removed. Although Applicants do not intend to be limited thereby, the DNA of the human mdr1 gene is quite large and contains extended 5' and 3' untranslated regions. Such extended regions may result in the generation of a reduced titer of viral vector particles, such as retroviral vector particles, which may be engineered with such DNA. Thus, removal of at least a portion(s) of the 5' and/or 3' untranslated regions may enable one to insert such DNA into a viral vector, such as a retroviral vector, whereby one generates an increased titer of retroviral particles. Within the scope of the present invention, up to the entire 5' untranslated region and/or up to the entire 3' untranslated region may be removed.

In accordance with another aspect of the present invention, there is provided DNA (or RNA) encoding a protein which provides for multidrug resistance, wherein the DNA includes the following sequence:
CAGGTATGC (SEQ ID NO:1)

At least one base is changed to a different base. Preferably at least one base of the GT doublet is changed.

In accordance with yet another aspect of the present invention, there is provided DNA (or RNA) encoding a protein which provides for multidrug resistance, wherein the DNA includes the following sequence:
ACATTTTCCTTCAGG (SEQ ID NO:2)

At least one base is changed to a different base. Preferably, at least one base of the AG doublet is changed.

In one embodiment, the DNA encoding a protein which provides for multidrug resistance includes a first sequence. CAGGTATGC, (SEQ ID NO:1) and a second sequence: ACATTTTCCTTCAGG (SEQ ID NO:2)

At least one base in the first sequence, and at least one base in the second sequence is changed to a different base. Preferably, at least one base of the GT doublet of the first sequence is changed, and at least one base of the AG doublet of the second sequence is changed.

The changed DNA or RNA sequence for a human mdr1 gene, or the changed DNA or RNA encoding a protein which provides for multidrug resistance, of the present invention may be cloned into any of a variety of expression vectors by genetic engineering techniques known to those skilled in the art. Such expression vectors include, but are not limited to, prokaryotic vectors, including bacterial vectors; eukaryotic vectors, such as, for example, yeast vectors and fungal vectors, and viral vectors, such as, but not limited to, retroviral vectors, and non-retroviral vectors such as, but not limited to, adenoviral vectors, adeno-associated viral vectors, and Herpes virus vectors. In one embodiment, the changed DNA (or RNA) is cloned into a retroviral expression vector. It is also contemplated that the changed DNA or RNA may be introduced into cells by means of non-viral systems and non-plasmid-based systems. Such systems include, but are not limited to, the injection of the naked changed DNA or RNA into a desired cell, liposomes which encapsulate such DNA or RNA, and which deliver such DNA or RNA to a cell, and the coupling of the DNA or RNA to a protein or other agent which binds to a cellular receptor.

Retroviral vectors which may be employed include those derived from Moloney Murine Leukemia Virus, Moloney Murine Sarcoma Virus, Rous Sarcoma Virus, Harvey Sarcoma Virus, and Spleen Necrosis Virus. In one embodiment, the retroviral vector may be derived from Moloney Murine Leukemia Virus and is one of the LN series of vectors, as described in Miller, et al., *Biotechniques,* Vol. 7, pgs. 980–990 (1989). Such vectors have a portion of the packaging signal derived from a mouse sarcoma virus, and a mutated gag initiation codon.

In another embodiment, the retroviral vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral vector includes each of these cloning sites.

When a retroviral vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

Examples of retroviral vectors having at least two restriction enzyme recognition sites having an average frequency of appearance in eukaryotic genes of less than once in 10,000 base pairs, and of the shuttle cloning vectors employed in transfering genes to such vectors are further described in PCT Application No. WO91/10728.

The vectors also include one or more promoters. Suitable promoters which may be employed include, but are not limited to, the retroviral LTR; the SV40 promoter; and the human cytomegalovirus (CMV) promoter described in Miller, et al., *Biotechniques,* Vol. 7, No. 9, pgs. 980–990 (1989), or any other promoter (e.g., cellular promoter such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

The vector may also further include a heterologous or foreign gene.

Heterologous or foreign genes which may be placed into the vectors of the present invention include, but are not limited to genes which encode cytokines or cellular growth factors, such as lymphokines, which are growth factors for lymphocytes. Other examples of foreign genes include, but are not limited to, genes encoding soluble CD4, Factor VIII, Factor IX, ADA, the LDL receptor, ApoI, tumor necrosis factors (TNF's) and ApoC.

Suitable promoters which may control the foreign genes include those hereinabove described.

The vector including the DNA of the present invention may be transduced into a suitable packaging cell line. Examples of suitable packaging cell lines include the PA317 cell line and the PE501 cell line (Miller, et al., 1989), and the PAT 2.4 cell line (U.S. application Ser. No. 792,281, filed Nov. 14, 1991.) Transduction of the packaging cell line may be accomplished by standard techniques such as electroporation or CaPO$_4$ precipitation. Vector particles generated from such producer cells may then be employed to generate a producer cell line, and to transduce cells (eg., eukaryotic cells such as mammalian cells), which may be administered to a host as part of a gene therapy procedure. Examples of cells which may be transduced include, but are not limited to, primary human cells such as primary human nucleated blood cells (such as leukocytes, and lymphocytes such as TIL cells, T-lymphocytes, and β-lymphocytes), tumor cells, endothelial cells, epithelial cells, keratinocytes, stem cells, bone marrow cells, hepatocytes, connective tissue cells, fibroblasts, mesenchymal cells, mesothelial cells, and parenchymal cells.

Upon transfection or transduction of a packaging cell line with a retroviral vector, it is essential that the producer cell line generate a sufficient titer of vector particles for gene therapy protocols. Selection for growth of such packaging or producer cells in the presence of colchicine has resulted in the isolation of producer clones with viral titers below what is currently adequate for clinical gene therapy protocols.

It is therefore another object of the present invention to provide a method of selecting producer cells which generate an acceptable titer of retroviral particles including a human mdr1 gene, and in particular for generating an adequate titer of retroviral particles suitable for inserting and expressing the mdr1 gene in primate cells, particularly in primate repopulating hematopoietic stem cells.

In accordance with an aspect of the present invention, there is provided a method of identifying cells which overexpress a gene encoding multidrug resistance (preferably such gene is the human mdr1 gene) in a cell population transduced with an expression vehicle including a gene which encodes a protein which provides for multidrug resistance (preferably such gene is the human mdr1 gene). The method comprises contacting the cell population with a staining material, and identifying the cells which overexpress the gene encoding a protein which provides for multidrug resistance (preferably the human mdr1 gene) based on differentiation of color among the cells of the cell population.

Such differentiation in color may be based on differences in color intensity between cells which overexpress the human mdr1 gene and cells which do not overexpress the human mdr1 gene (for example, cells which contain vectors including the human mdr1 gene, whereby such cells overexpress the human mdr1 gene, may be brighter or duller than those cells which do not contain vectors including the human mdr1 gene, whereby such cells which express the human mdr1 gene at normal levels or do not express the gene); or differences in color or shades of color between cells which contain vectors including the human mdr1 gene, and thereby overexpress the human mdr1 gene, and cells which do not contain vectors including the human mdr1 gene, and thereby express the human mdr1 gene at normal levels or do not express the human mdr1 gene. Alternatively, cells which contain vectors including the human mdr1 gene, and thereby overexpress the human mdr1 gene may change color after staining, while cells which do not contain vectors which include the human mdr1 gene do not change color after staining.

The term "overexpress" as used herein, means that the gene encoding multidrug resistance is expressed at a level above that which is expressed by a normal human cell. In normal human cells, the mdr1 gene is expressed at low levels or is not expressed. In cells transduced with an expression vehicle including the mdr1 gene, the expression level of the mdr1 gene is considerably increased, and thus, the mdr1 gene is "overexpressed."

Applicants have found that, by identifying cells which overexpress the human mdr1 gene in a cell population transduced with infectious viral particles which include the human mdr1 gene, in accordance with the method of the present invention, Applicants have been able to isolate clones which produce higher viral titers than clones selected with drugs such as colchicine, for example.

In one embodiment, the staining material is a fluorescent dye. Fluorescent dyes which may be employed include, but are not limited to, rhodamine 123, 3,3'-diethyloxacarbocyanine iodide (DiOC$_2$), and 3,3'-diethyloxadicarbocyanine iodide (DODC iodide).

In one embodiment, the fluorescent dye is rhodamine 123. Rhodamine 123 ordinarily concentrates within the mitochondria of cells, but can be effluxed from the cell by p-glycoprotein. Cells stained with rhodamine 123 that do not express p-glycoprotein or express p-glycoprotein at normal or lower than normal levels appear "bright" by fluorescence microscopy or by FACS analysis, whereas cells that overexpress p-glycoprotein appear "dull," even if small quantities of p-glycoprotein are expressed. (Chaudhary, et al., *Cell*, Vol. 66, pgs. 85–94 (Jul. 12, 1991)). Thus, producer cells or other cells which have incorporated and express a functional human mdr1 gene may be distinguished from non-transformed cells on the basis of this "dull" staining phenotype.

Such a method may also be employed to determine viral titer of human mdr1 retrovirus producer cell lines. In one embodiment, a defined number of target cells are exposed to serial dilutions of a viral supernatant produced by a defined number of producer cells. After infection (eg., at about 48 hrs. after infection), the cells are stained with rhodamine 123 and allowed to efflux the dye. The proportion of "dull" cells can be visually estimated by fluorescence microscopy, or accurately quantitated by scoring a defined number of individual cells by FACS analysis. Because the proportion of cells overexpressing p-glycoprotein is known, it is possible to calculate accurately the minimum number of infectious viral particles present in a known volume of viral supernatant.

Although it has been demonstrated that retroviral vectors may be used to transfer and express the mdr1 gene in cultured cells (*Proc.Nat.Acad.Sci.*, Vol. 85, pgs. 1595–1596 (1988)); in murine repopulating hematopoietic stem cells (Sorrentino, et al., *Science*, (in press)), and in murine hematopoietic progenitors in vitro (McLachlin, et al., *J.Nat.Canc.Inst.*, Vol. 82, pgs. 1260–1263 (1990)), there has been no demonstration of transfer and expression of the mdr1 gene in primate cells, and in particular in primate stem cells capable of reconstituting transplant recipients.

Thus, in accordance with an aspect of the present invention, there is provided a primate cell which is genetically engineered with DNA (RNA) which encodes a protein which provides multidrug resistance. The DNA (RNA) may be any DNA (RNA) which encodes a protein which provides multidrug reistance or the changed DNA or RNA sequences which are hereinabove described.

Applicants have discovered that by selecting for cells transduced with a gene encoding multidrug resistance in accordance with the selection method hereinabove described, one is able to obtain producer cells which generate a sufficient titer of infectious viral particles which provide for the transfer and expression of multidrug resistance genes in primate cells, in particular in primate repopulating hematopoietic stem cells.

Primate cells which may be genetically engineered with such DNA (RNA) include, but are not limited to, primate bone marrow cells, preferably enriched primate bone marrow cells, and hematopoietic progenitor (CD34+) cells or hematopoietic stem cells (in particular, primate repopulating hematopoietic stem cells), and human primary cells. The hematopoietic stem cells may also be CD33⁻ and HLA-DR$^{low}$. (Chaudhary, et al., 1991) The primate cells may be obtained from humans or other primates, such as monkeys, for example.

This aspect of the present invention is particularly applicable to the use of primate repopulating hematopoietic stem cells which are genetically engineered with DNA (RNA) which encodes a protein which provides multidrug resistance. Such stem cells give rise to bone marrow cells and may be administered, for example, to a patient who has undergone chemotherapy and/or radiation treatment in order to regenerate healthy bone marrow cells in the patient. Thus Applicants have devised a system for identifying producer cells which generate a sufficient titer of viral particles including a gene encoding multidrug resistance, whereby such viral particles may be used to infect primate repopulating hematopoietic stem cells, which may then be administered to a patient in order to regenerate bone marrow in said patient, wherein such regenerated bone marrow is resistant to the toxic effects of chemotherapy.

In one embodiment, bone marrow cells are harvested by needle aspiration from a primate, and purified by positive selection for cells expressing the CD34 antigen. CD34 selected cells are enriched 50–100 fold in clonogenic hematopoietic progenitors and contain all of the repopulating stem cells. Alternatively, the bone marrow cells may be purified in accordance with the procedures described in U.S. Pat. No. 5,061,620.

The CD34+ cells are incubated in vitro in the presence of stimulatory hematopoietic growth factors and in the presence of retroviral supernatant containing infectious viral particles which include a multidrug resistance gene. The viral particles are generated from a producer cell line selected in accordance with the selection procedure hereinabove described. After incubation, the cells are transplanted into recipients suitably treated to receive a bone marrow transplant. After transplantation, bone marrow cells, peripheral blood leukocytes, purified granulocytes, and T-lymphocytes are assayed for presence and expression of the introduced mdr1 gene.

The invention will be described with respect to the following examples; however, the scope of the present invention is not intended to be limited thereby.

BRIEF DESCRIPTION OF THE DRAWINGS

The invention now will be described with respect to the drawings, wherein:

FIG. 2 is a DNA sequence of the multiple cloning site in pG1;

FIG. 4 is the cDNA sequence of the human mdr1 gene;

FIG. 5 is a plasmid map of pGEM-2;

FIG. 6 is a restriction map of pMDR 2000XS;

EXAMPLE 1

A. Construction of plasmid pG1

Figure 1:
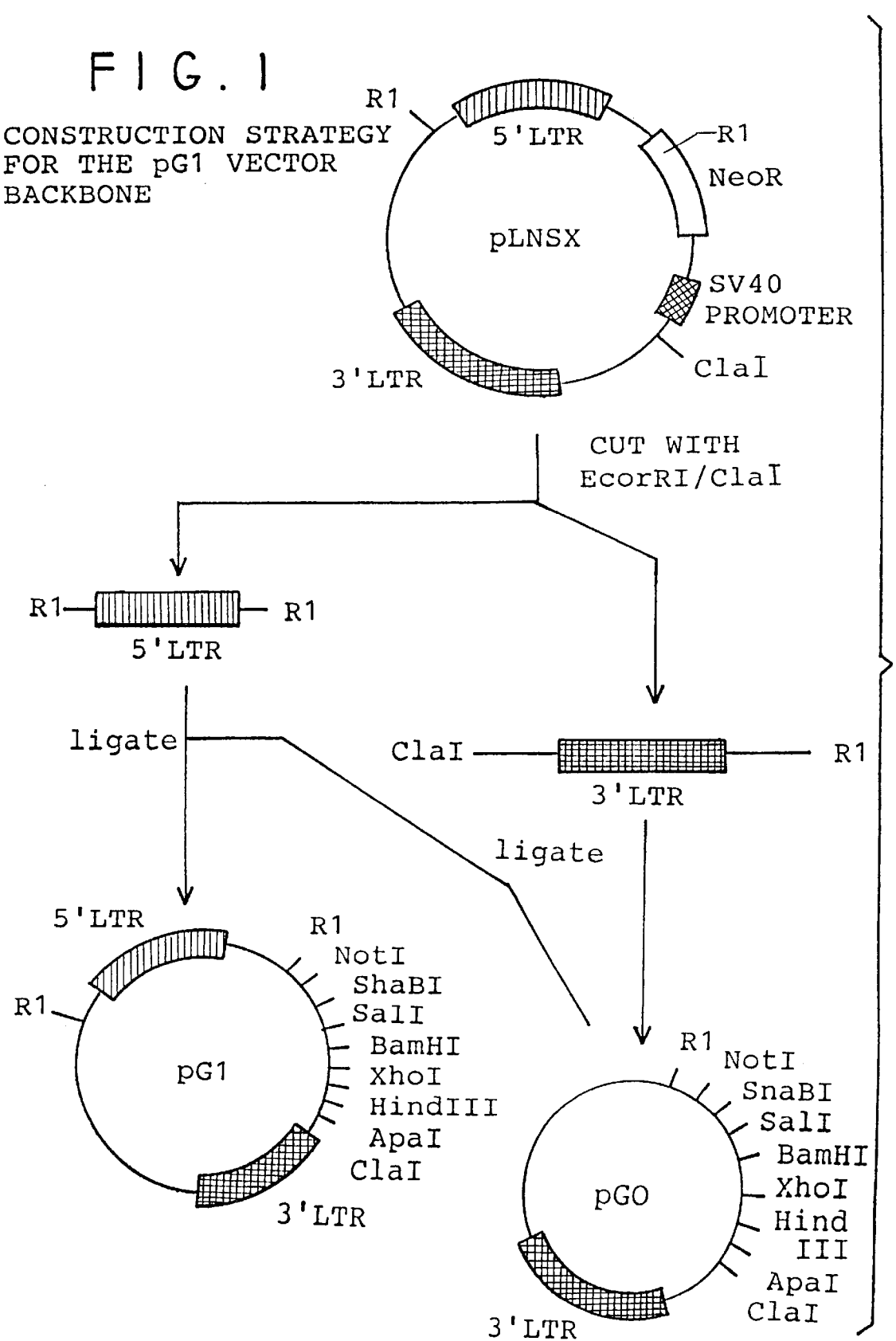
FIG. 1 is a schematic of the construction strategy for pG1.
Figure 3:
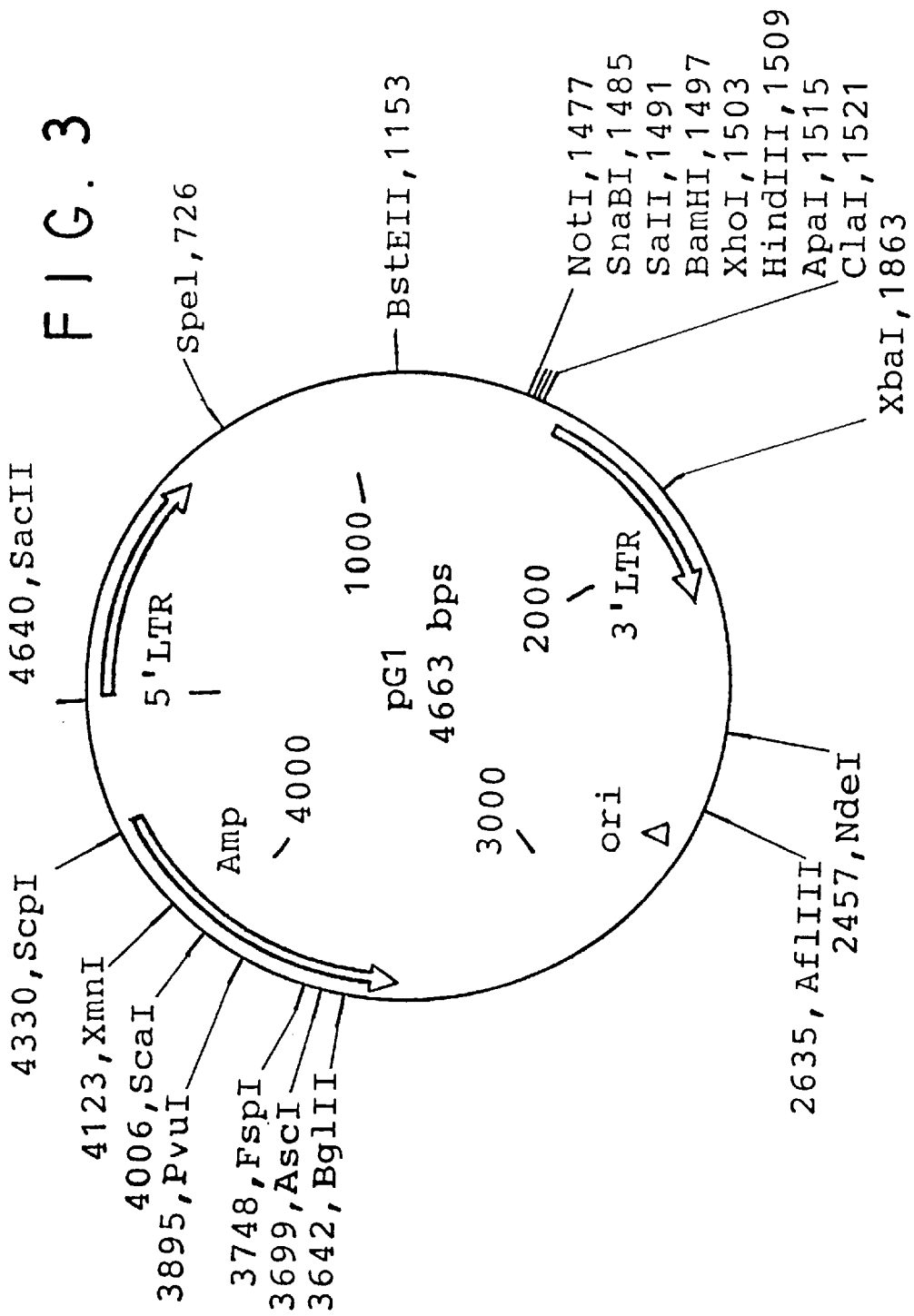
FIG. 3 is a plasmid map of pG1.

Plasmid pG1 was constructed from pLNSX (Palmer et al., Blood, 73:438–445; 1989). The construction strategy for plasmid pG1 is shown in FIG. 1. The 1.6 kb EcoRI fragment, containing the 5' Moloney Sarcoma Virus (MoMuSV) LTR, and the 3.0 kb EcoRI/ClaI fragment, containing the 3' LTR, the bacterial origin of replication and the ampicillin resistance gene, were isolated separately. A linker containing seven unique cloning sites was then used to close the EcoRI/ClaI fragment on itself, thus generating the plasmid pG0. The plasmid pG0 was used to generate the vector plasmid pG1 by the insertion of the 1.6 kb EcoRI fragment containing the 5' LTR into the unique EcoRI site of pG0. Thus, pG1 (FIG. 3). consists of a retroviral vector backbone composed of a 5' portion dervied from MoMuSV, a short portion of gag in which the authentic ATG start codon has been mutated to TAG (Bender et al. 1987), a 54 base pair multiple cloning site (MCS) containing from 5' to 3' the sites EcoRI, NotI, SnaBI, SalI, BamHI, XhoI, HindIII, ApaI, and ClaI, and a 3' portion of MoMuLV from base pairs 7764 to 7813 numbered as described in (Van Beveren et al., Cold Spring Harbor, Vol. 2, pg. 567, 1985). (FIG. 2). The MCS was designed to generate a maximum number of unique insertion sites, based on a screen of non-cutting restriction enzymes of the pG1 plasmid, the neo$^R$ gene, the β-galactosidase gene, the hygromycin$^R$ gene, and the SV40 promoter.

B. Construction of pG1MD1 pMDR2000 (Ueda, et al., PNAS, Vol. 84, pgs. 3004–3008 (May 1987)), which contains an mdr1 cDNA sequence (SEQ ID NO:18) (FIG. 4) described in PCT application number WO87/05943, wherein the first 282 bp of the untranslated 5' region and the last 23 bp of the untranslated 3' region of the cDNA sequence have been removed, was cut with SacI and EcoRI, and was inserted into a multiple cloning site of SacI and EcoRI digested pGEM2 (FIG. 5.) (Promega, Madison, Wis.) to form pGEM2MDR. pGEM2MDR was then cut with SmaI at the 5' end of the multiple cloning site and a SacII linker having a length of 8 bp was inserted. At the 3' end of the plasmid, the plasmid was cut with EcoRI and a 12 bp XhoI linker was inserted. The resulting plasmid was pMDR2000XS. (FIG. 6.)

Plasmid pMDR2000XS was then cut at the 5' end of the cDNA sequence for mdr1 with HhaI, and at the 3' end of the cDNA sequence for mdr1 with HaeII, and a 3,845 bp fragment was removed. Such cutting removed an additional 131 bp from the 5' end, and an additional 384 bp from the 3' end of the cDNA. A linker was then added to the 3' sequence to reconstitute the amino acids that were cut off by cutting with HaeII and to add the TGA stop (or termination) codon back into the sequence. The linker has four restriction enzyme sites, HpaI, XhoI, BglII, and ClaI, and has the following sequence:

5'-A G T G A A C T C T G G T T A A C T C C
     10 20
A C T C G A G C A C A G A T C T G G A
     30
C A T C G A T A C T C (SEQ ID NO:3)
     40 50

Figure 7:
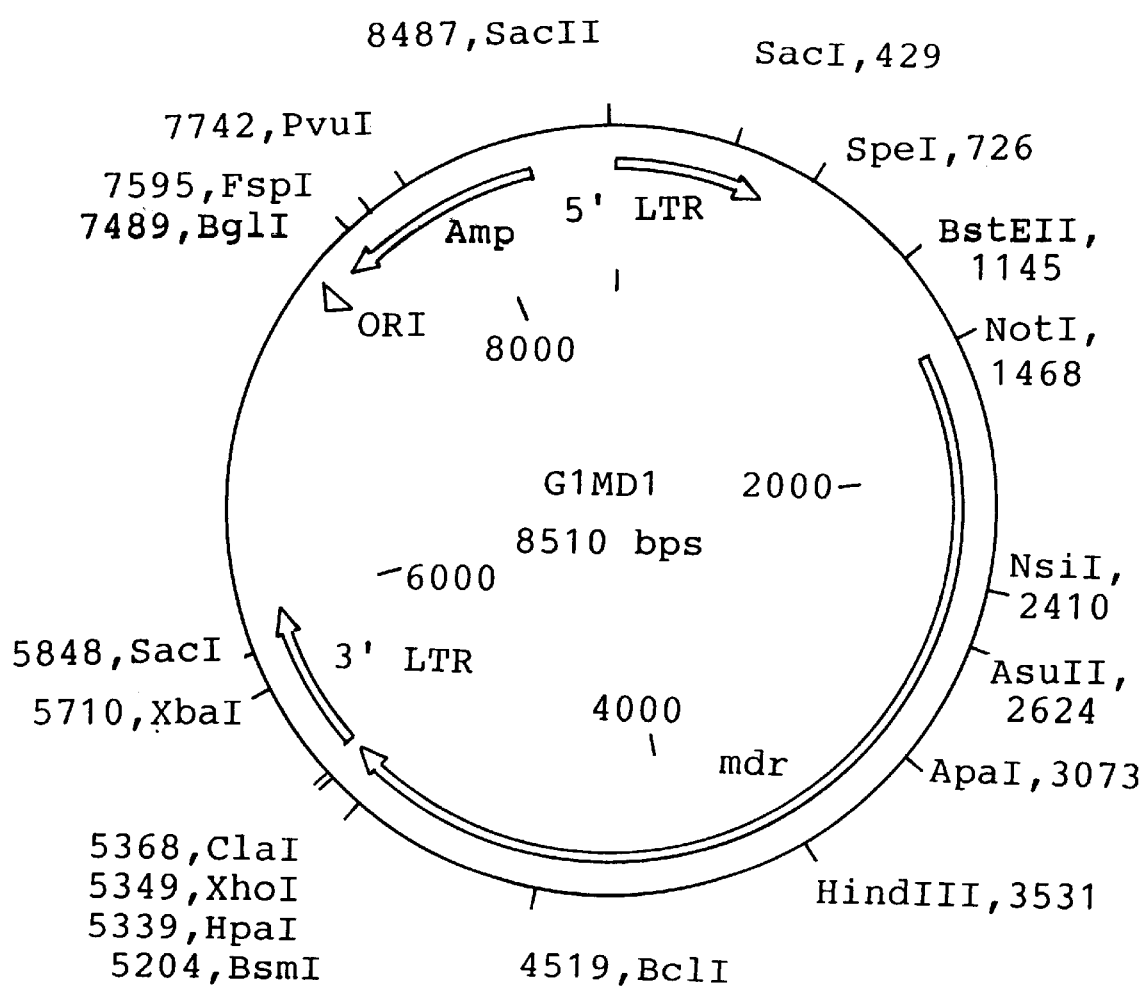
FIG. 7 is a plasmid map of pG1MD1.

Bases 12–17 are recognized by HpaI, bases 22–27 are recognized by XhoI, bases 31–36 are recognized by BglII, and bases 41–46 are recognized by ClaI.

pG1 was then cut with SnaBI and ClaI, and the mdr1 fragment containing the added linker was cut with ClaI and inserted into the SnaBI and ClaI digested pG1 to form pG1MD1 (FIG. 7.)

C. Changing codons 113,185, and 773 of the mdr1 gene

Changing the mdr1 gene in pG1MD1 such that codon 113 is changed from AGG to AGA, codon 185 is changed from GTT to GGT (whereby Val is changed to Gly in the resulting expressed p-glycoprotein), and codon 773 is changed from CAG to CAA may be accomplished by either of the following strategies.

1. Introduction of point mutations into G1MD1 by site-directed mutagenesis pG1MD1 is digested with NotI and XhoI, and a NotI-XhoI fragment is cloned into the phagemid pBluescriptSK+ (Stratagene). The resulting subclone is transformed into *E. coli* strain CJ236 (Biorad). A 5 ml culture is grown at 37° C. overnight in LB broth with 200 μg/ml ampicillin and 30 μg/ml chloramphenicol. 2.5 ml of this culture is then added to 25 ml of fresh media with the same antibiotics, and grown at 37° C. until the O.D.600 of the culture reaches 0.3. Helper phage R408 (Stratagene) is then added at a multiplicity of infection of 20 to the culture. The culture is then incubated by vigorous shaking for 8 hours. The culture is then harvested by centrifugation at 17,000× g for 15 minutes at 4° C. The supernatant fluid is harvested and spun again at 17,000× g for 15 minutes at 4° C. The supernatant is then harvested and measured for volume.

A ¼ volume of a solution containing 3.5M ammonium acetate and 20% polyethylene glycol is then added to the supernatant to precipitate the phage. The solution and supernatant mixture is incubated at room temperature for 15 minutes. The precipitate is then centrifuged at 11,000× g for 15 minutes at 4° C. The resulting pellet is suspended in 400 μlTE (10 mM Tris, 1 mM EDTA) and extracted with phenol/chloroform until the interphase is clear. The DNA (phage/template) is then ethanol precipitated by standard procedures.

2 ng of the following antisense oligonucleotides:

(a) 5'-T C T G T A C T G G T C T A T A C G G A T A A T
10 20
A A T G T C-3'(SEQ ID NO:4)
30 wherein the TCT sequence (nucleotides 11–13) will provide for a change of codon 139 from AGG to AGA;

(b) 5'-C T A A T T A C T T C C A T A A C C A C T G T T
10 20
T T A A C C-3'(SEQ ID NO:5)
30 wherein the CCA sequence (nucleotides 11–13) will provide for a change of codon 185 from GTT to GGT (whereby Val 185 is changed to Gly 185); and (c) 5'-G T A A A A A G G A A G T T C C A A A G T G T A
10 20
A A C C G T-3'(SEQ ID NO:6)
30 wherein the GTT sequence (nucleotides 12–14) will provide for a change of codon 733 from CAG to CAA, and 200 ng of the phage/template DNA are then mixed in 10 μl of TE. The mixture is heated to 70° C., and then allowed to cool slowly to room temperature in order to anneal the oligonucleotides to the template. Deoxynucleotide triphosphates are then added to the mixture, followed by T4 DNA polymerase, T4 ligase, 10× synthesis buffer, and water to make the volume 20 μl. The mixture is then placed on ice for 5 minutes, then at 25° C. for 5 minutes, and then at 37° C. for 90 minutes.

At the end of the 90 minute incubation, 90 μl of TE is added and 5 μl of the resulting mixture is used to transform *E. coli* strain DH5α.

Mutagenized clones are then identified by colony hybridization with the oligonucleotides (a), (b), and (c) hereinabove described. The identified and changed mdr1 gene is then cut out of pBluescript with NotI and XhoI and cloned into pG1 cut with NotI and XhoI to form pG1MD3.

2. Introduction of Point Mutations into G1MD1 by PCR Based Strategy

The cryptic splice donor site and the Gly to Val point mutation in codon 185 are contained within a NotI to ApaI restriction fragment of pG1MD1. This NotI to ApaI fragment can be excised, purified, and subcloned into a pUC based cloning vector called pUC007 (Sorrentino, et al., *Nucleic Acids Research*, Vol. 18, No. 9, pgs. 2721–2731 (1990)) that contains a synthetic polylinker multiple cloning site. The vector is prepared by partial digestion of pUC007 with EspI, and complete digestion with ApaI. The insert is prepared by digesting with NotI, blunting the NotI digested end with Klenow, and then digesting with ApaI. Following ligation, the abutment of the blunt FspI site with the blunted NotI site will recreate a NotI site that can be used to excise a NotI to ApaI fragment.

Following subcloning of the NotI to ApaI fragment into pUC007 (to form pMD1NA), the cryptic splice donor site and the codon 185 point mutation will be contained within a unique BstXI to MscI fragment. A strategy of overlapping or "recombinant" PCR to introduce point mutations into this BstXI to MscI fragment is employed. (Higuchi, *PCR Protocols: A Guide to Methods and Applications*, Innis, et al., eds, San Diego, Academic Press, pgs. 177–183 (1990)). Three sets of PCR primers are made. One set of complementary primers (SD-A and SD-B), which have the following sequences:

SD-A: GGAAGACATGACCAGATATGCCTATTATT-ACAG (SEQ ID NO:7)

SD-B: CTGTAATAATAGGCATATCTGGTCATGTCTTCC (SEQ ID NO:10)

are centered around the cryptic splice donor site, and differ from the sequence of G1MD1 at only one base, located in codon 139 of the mdr1 gene, wherein AGG is changed to AGA. This difference inactivates the splice donor site, although the amino acid is not changed. The second set of primers (C185-A and C185-B), which have the following sequences:

C185-A: CTCTAAGATTAATGAAGGTATTGGTGA-CAAAATTG (SEQ ID NO:9)

C185-B: CAATTTTGTCACCAATACCTTCAT-TAATCTTAGAG (SEQ ID NO:10)

are centered at the codon 185 mutation of the mdr1 gene and will differ from the sequence of G1MD1 only at the point mutation wherein codon 185 is changed from GTT to GGT. This difference corrects the point mutation in the cDNA sequence (FIG. 7) and encodes Gly in the final construction. The third set of primers flank the BstXI and MscI restriction sites. These primers (5'Bst and 3'Msc), which have the following sequences:

5'Bst: ATCGCGGATCCATGGTGGTGGGAACTTTGGC (SEQ ID NO:11)

3'Msc: CATCCGGAATTCAGCTGACAGTC-CAAGAACAGGACTGATG (SEQ ID NO:12)

overlap the BstXI and MscI sites, respectively, and also incorporate another flanking restriction site that will allow the PCR fragment to be conveniently subcloned. Using the technique of "recombinant" PCR, three separate PCR reactions will be initiated, using MD1NA as the template DNA. In these reactions, a "proofreading" thermostable DNA polymerase, such as Vent polymerase marketed by New England BioLabs, is used to avoid misincorporation of nucleotides, as can occur with high frequency when Taq polymerase is used. In the first PCR reaction, the two primers are 5'Bst and SD-B, and amplify the sequence from the BstXI site to the cryptic splice donor site. In the second PCR reaction, the two primers are SD-A and C185-B, and amplify the sequence from the splice donor to the codon 185 mutation. In the third PCR reaction, the primers are C185-A and 3'Msc, and amplify the sequence from the codon 185 mutation to the MscI site. Following ten cycles of amplification, the product of these three reactions is purified away from unused primers, nucleotides, and buffer. The purified PCR products are mixed together, and then amplified for an additional 10 to 20 cycles with a "proofreading" polymerase such as Vent polymerase, using the 5'Bst and 3'Msc primers. This final PCR reaction results in an amplified PCR product that extends from the BstXI site to the MscI site, and has introduced point mutations into the cryptic splice donor site and the mutant codon 185. Using the flanking restriction sites, the PCR product is digested with BamHI and EcoRI and is subcloned into a pUC based vector prepared by digestion with BamHI and EcoRI using inactivation of the lacZ gene to identify vectors that have incorporated the insert. This construct is referred to as pMD1BM and is used to transform bacteria. Bacteria that contain the plasmid carrying the desired point mutations will be identified by hybridization to allele specific oligonucleotides. MD1BM plasmid DNA isolated from these subclones is then sequenced, using standard M13 sequence primers, to confirm that the desired mutations have been introduced, and that no additional mutations have been created.

After sequencing, a BstXI to MscI fragment is excised from MD1BM and subcloned into a vector prepared by digestion of MD1NA with BstXI and MscI. This plasmid is referred to as MD1NA-C. A NotI to ApaI fragment is excised from MD1NA-C and inserted into a vector prepard by digestion of G1MD1 with NotI and ApaI. The resulting plasmid is referred to as pG1MD1A, and contains a cDNA for a human mdr1 gene that has a conservative point mutation inactivating a cryptic splice donor site, as well as another point mutation that causes a reversion in the amino acid sequence at codon 185 to the wild type sequence.

The cryptic splice acceptor site can be corrected using a similar PCR based strategy. A HindIII to XhoI fragment containing the cryptic splice acceptor can be subcloned directly into the HindIII and XhoI sites of pUC007 (This plasmid is designated pMD1HX). The cryptic splice acceptor is contained within an XmnI to KpnI fragment. Recombinant PCR is then used to introduce a point mutation into the cryptic splice acceptor site. One primer set is required. The first primer (5'Xmn) having the following sequence:
5'Xmn:
   ATCGCGGATCCGGAATTATTTCTTTTAT-
   TACATTTTTCCTTCAAGGTTTCACATTTGG (SEQ ID NO:13)
overlaps the XmnI site and extends past the cryptic splice acceptor. This primer will be identical to the sequence in G1MD1 except at one base in codon 773 wherein codon 773 is changed from CAG to CAA, which inactivates the splice acceptor site. The amino acid encoded by codon 773, however, is unchanged. This primer also incorporates a flanking BamHI site to facilitate subcloning of the PCR product. The second primer (3'Kpn), having the following sequence:
3'Kpn:
   CTCAAAGAGTTTCTGTATGGTACC (SEQ ID NO:14)
overlaps the KpnI site. These primers are used to amplify a fragment of DNA from pMD1HX with a proofreading polymerase such as Vent polymerase. This PCR product is digested with BamHI and KpnI and subcloned into the BamHI and KpnI sites of a cloning vector such as pUC19 (This plasmid is designated pMD1XK). This plasmid is used to transform bacteria. Subclones containing the "corrected" sequence are identified by allele specific oligonucleotide hybridization and sequencing as described above. Subsequently, an XmnI to KpnI fragment from pMD1XK is subcloned into the XmnI and KpnI sites of pMD1HX (The resulting plasmid is designated pMD1HX-C). Finally, a HindIII to XhoI fragment from MD1HX-C is subcloned into the HindIII and XhoI sites of pG1MD1 to form pG1MD1B, which contains a cDNA for the mdr1 gene that has a conservative point mutation inactivating a cryptic splice acceptor site.

In order to construct a plasmid that contains a cDNA for an mdr1 gene with mutations introduced into the cryptic splice donor site, codon 185, and the cryptic splice acceptor site, a HindIII to XhoI fragment is excised from pG1MD1B. This fragment is then subcloned into a vector prepared by digesting pG1MD1A with HindIII and XhoI. The resulting plasmid is referred to as pG1MD1AB.

D. Generation of producer cell lines from pG1MD3 and pG1MD1AB

The vectors pG1MD3 and pG1MD1AB, described in Example 1, which contain the changes in codon 1113 (in the splice donor site), in codon 773 (in the splice acceptor site), and in codon 185 (wherein Val 185 is changed to Gly 185), may be placed into a packaging cell line to generate vector particles, and to generate producer cell lines.

Vector producer cell lines are prepared using established protocols. The packaging cell line PE501 (Miller and Rosman, *Biotechniques* 7:980–990 (1989)) or cell line GP+E86 is plated at a density of $5 \times 10^5$ cells per 100 mm plate and the following day purified vector DNA is introduced using standard $CaPO_4$ precipitation (Wigler et al., *Cell* 14725–731 (1978)). For each plate of cells to be transfected, 20–40 µg of vector DNA is prepared with a co-precipitate consisting of 0.25M $CaCl_2$/1 mM Hepes (pH 7.2) and 140 mM NaCl, 0.75 mM $Na_2HPO_4$, 25 mM Hepes (pH 7.2). The DNA/precipitate is allowed to sit at room temperature for 30 min and then added (1 ml/plate) to the cells in tissue culture medium (DMEM+10% fetal Bovine serum) for an overnight incubation. The medium is changed to fresh DMEM+serum the following morning. The transfected cells are allowed to grow to near confluence for the next 48 hours, at which point virus supernatant is collected to infect a separate population of PA317 or GP+AM12 vector packaging cell lines at a density of $1 \times 10^5$ cells per 100 mm plate seeded 24 hours prior to infection. The standard infection conditions include undiluted virus supernatant, filtered through a 0.2 uM membrane, to which 8 ug/ml polybrene is added. After overnight incubation for 16 hours, the medium is changed to DMEM and 10% Fetal Bovine Serum, and grown until such cells are selected with rhodamine 123. The polyclonal population of GP+Am12 or PA 317 cells are incubated with rhodamine 123 at a concentration of 1 microgram per ml at 37° C. for 30 minutes.

Following staining, the cells are allowed to efflux the dye for two hours in medium that did not contain rhodamine. The cells are then trypsinized, and $5\times10^6$ cells are sorted on a Coulter EPICS Elite FACS machine, with excitation at 480 nm and fluorescence measured at 525 nm. The bright cells, which did not express p-glycoprotein, are discarded. Cells that are "dull" following rhodamine staining express p-glycoprotein and are collected for further processing.

Example 2

Selection of producer cells generating high titers of viral particles including an mdr1 gene PA317 (amphotropic) packaging cells were transfected by the $CaPO_4$ method with pG1MD1. 48 hours later, supernatant from the transfected PA317 cells (Miller, et al., 1989) was filtered and added to GP+E86 (ecotropic) packaging cells in the presence of 6 micrograms per ml of polybrene. 24 hours following infection with this transient supernatant, drug selection with colchicine at a concentration of 60 ng/ml was applied. Afte two weeks of drug selection, individual drug resistant GP+E86 clones were isolated and characterized for production of recombinant retrovirus using an RNA slot blot technique (Bodine, et al., *Proc. Nat. Acad. Sci.*, Vol. 87, pgs. 3738–3742 (May 1990)). The ecotropic MDR producer clone with the highest apparent titer, referred to as E4, was used in the subsequent experiments.

Figure 8A:
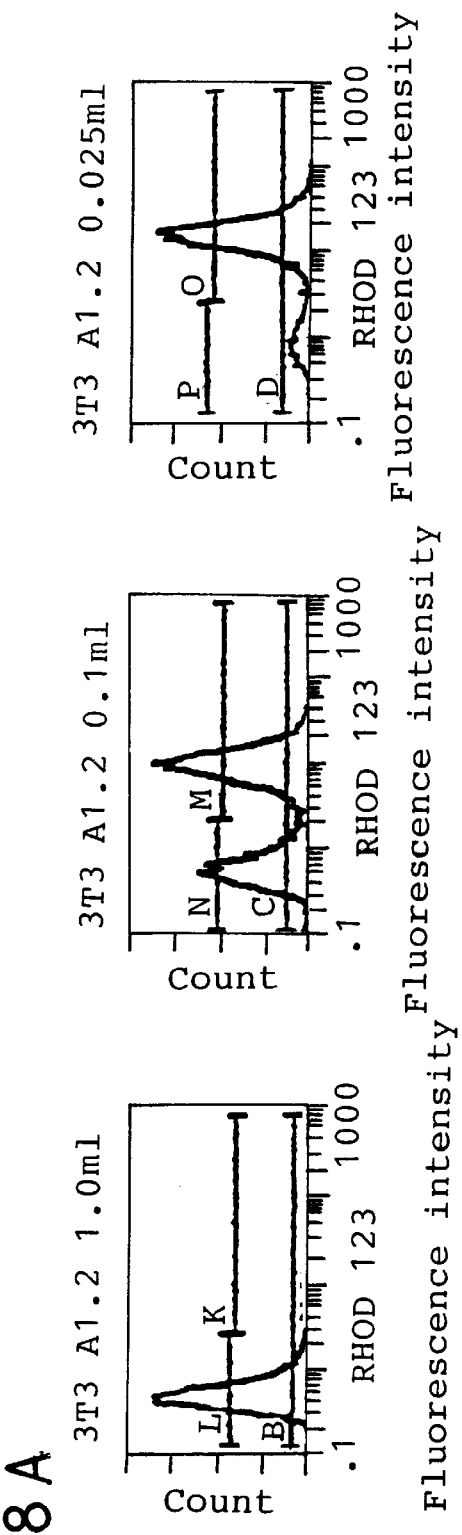
FIGS. 8A and 8B are measures of the results of rhodamine titering assays for the presence of the human mdr1 gene in viral producer cells.

Filtered viral supernatant from the ecotropic E4 producer cell line was used to infect the amphotropic packaging cell line GP+Am12 (Markowitz, et al., *Virology*, Vol. 167, pgs. 400–406 (1988), Markowitz, et al., *J. Virol.*, Vol. 62, pgs. 1120–1124 (1988)) In this particular experiment, the GP+Am12 line was exposed to a total of 6 viral supernatants over the course of one week. Following infection, GP+Am12 cells that had been transduced with the MDR virus and expressed p-glycoprotein were selected by FACS using rhodamine 123 staining to identify transduced cells. The polyclonal population of GP+Am12 cells was incubated with rhodamine 123 at a concentration of 1 microgram/ml at 37 degrees C. for 30 minutes. Following staining, the cells were allowed to efflux the dye for two hours in medium that did not contain rhodamine. The cells were then trypsinized, and $5\times10^6$ cells were sorted on a Coulter EPICS Elite FACS machine, with excitation at 480 nm and fluorescence measured at 525 nm. The bright cells, that did not express p-glycoprotein, were discarded. Cells that were "dull" following rhodamine staining express p-glycoprotein and were collected for further processing. In this particular experiment, the "dull" population was further subdivided into three groups ("A", "B", and "C") based on the degree of "dullness." These dull cells were plated at limiting dilution. A total of 1500 wells were plated at two concentrations of one cell per two wells and one cell per five wells. Following two weeks in culture, individual subclones were expanded and characterized for estimated viral titer using the RNA slot blot technique on filtered viral supernatant. Ten clones were identified with the highest production of packaged and secreted viral RNA. These clones were subsequently characterized for viral titer using the rhodamine titering protocol. In this protocol, 10 ml of media is conditioned by $5\times10^6$ producer cells for 24 hours. The supernatant is filtered, and dilutions of the filtered supernatant are used to infect a target cell population, in this case 3T3 cells. To infect 3T3 cells a total of 10 ml of media containing viral supernatant and 6 micrograms per ml of polybrene (or 5 micrograms per ml of protamine sulfate) is added to $10^6$ target cells on a 10 cm plate for a period of 48 to 72 hours. The plate of infected 3T3 cells is then stained with rhodamine 123 at 1 microgram/ml at 37 degrees for 30 minutes, and then destained for two hours in media without rhodamine. The plate is then trypsinized and analyzed by FACS to quantitate the proportion of cells that express the "dull" phenotype. Alternatively, the plate of cells can be directly examined by fluorescence microscopy. This information is then used to calculate viral titer. For example, if 0.1 ml of viral supernatant is able to confer the "dull" phenotype to 10 percent of $10^6$ cells, then 0.1 ml of viral supernatant contains a minimum of $1\times10^5$ viral particles, and 1 ml of viral supernatant contains a minimum of $1\times10^6$ viral particles. As shown in FIG. 8A, as the volume of viral supernatant from producer clone G1MD1 A1.2 which contacts the 3T3 cells increases from 0.025 ml to 0.1 ml, and then to 1.0 ml, the height of the left peak, which corresponds to the number of cells having the "dull" phenotype, and which therefore have a lower fluorescence intensity, increases, while there is a decrease in the number of cells having the "bright" phenotype (such cells have a higher fluorescence intensity) as evidenced by the decrease in the size of the right peak. Using this assay, a identified GP+Am clone with a titer of $4\times10^6$ viral particles per ml was identified. This producer clone was designated G1MD1 A1.2.

Example 3

Figure 8B:
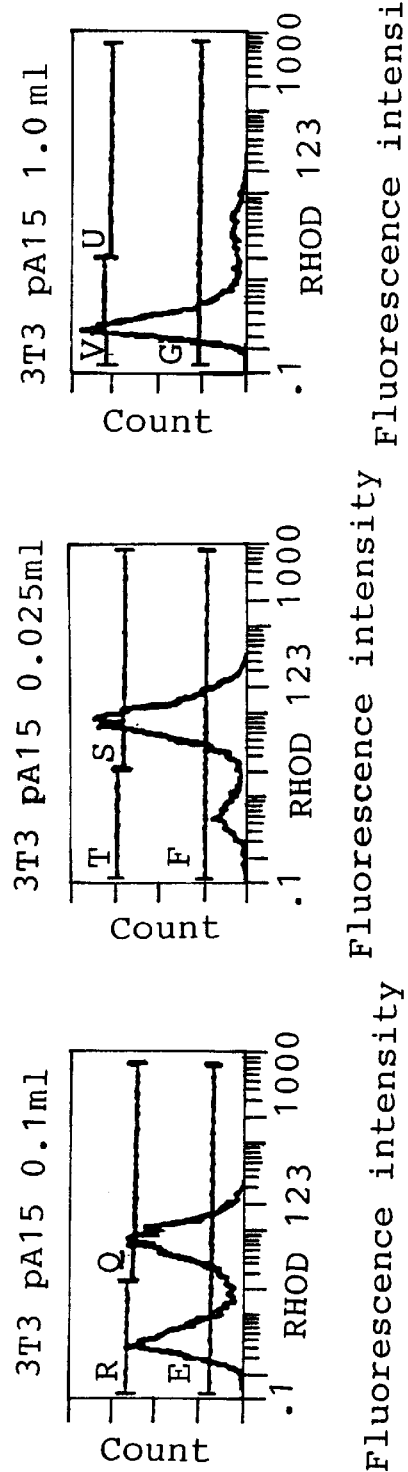

PA317 cells (Miller, et al., 1989), obtained from the ATCC and selected in HMT medium (following the protocol suggested by the ATCC) were transduced with viral supernatant from the ecotropic E4 producer cell line obtained as hereinabove described in Example 2. The PA317 packaging cell line was serially infected with E4 viral supernatant over the course of 10 days until 100% of the cells in the population expressed the rhodamine "dull" phenotype. The phenotype was evaluated by fluorescence microscopy and FACS analysis on aliquots of the population. A total of 13 exposures to viral supernatants were used. The population of infected PA317 cells were directly plated at limiting dulution. A total of 1,500 wells were plated at dilutions of 1:3 and 1:5 cells per well. Individual clones were isolated and subsequently scored for viral RNA production using the slot blot assay. The subclones with the highest production of viral RNA were then analyzed by the rhodamine titering assay hereinabove described in Example 2. As shown in FIG. 8B, as the volume of viral supernatant from producer clone PA15 which contacts the 3T3 cells increases from 0.025 ml to 0.1 ml and then to 1.0 ml, the height of the left peak, which corresponds to the number of cells having the "dull" phenotype, and which therefore have a lower fluorescence intensity, increases, while there is a decrease in the number of cells having the "bright" phenotype (such cells have a higher fluorescence intensity) as evidenced by the decrease in the size of the right peak. One subclone, PA15, was identified which had a titer of $5\times10^6$ viral particles per ml.

Example 4

Bone marrow cells were harvested from the posterior iliac crests and femurs of 3–4 kg juvenile rhesus monkeys (*Proc. Natl. Acad. Sci. USA*, Vol. 87, pgs. 3738–3742 (1990)). The cells are aspirated into Dulbecco's Modified Eagle's Medium (DMEM) containing 2% fetal calf serum and 10 units of heparin/ml. Five days before the bone marrow harvest, the animals receive 5-fluorouracil (70 mg/kg) as a single intravenous bolus. During the bone marrow harvest procedure, the animal receives 100 ml of autologous red cells to replace the volume of blood that is removed. Prior to the bone marrow harvest, an in-dwelling central venous catheter is established by standard surgical techniques.

After harvest, the bone marrow was diluted with Hank's Buffered Saline Solution (HBSS) and passed through wire mesh to remove clumps of cells. Mononuclear cells were isolated by density gradient centrifugation using Ficoll-Paque. Cells expressing the CD34 antigen are isolated by immunoselection (*Science,* Vol. 242, pgs. 919–922 (1988)) using the magnetic bead technology. $2-4\times10^9$ total bone marrow cells are recovered by the harvest procedure. Approximately 20% of these cells are recovered as the mononuclear cell preparation and 2–3% of these cells are recovered by immunoselection. Thus a total of $2-4\times10^7$ CD34 cells are obtained at the time of bone marrow harvest. These were incubated at an initial concentration of $5\times10^5$ cells/ml for 36 hours in DMEM, 15% fetal calf serum, penicillin-streptomycin, and 2× glutamine. The following hematopoietic growth factors were added: Stem Cell Factor (100 ng/ml), interleukin-3(50 ng/ml) and interleukin-6 (50 ng/ml). After 36 hours, the cells were recovered by centrifugation and resuspended at $5\times10^5$ cells/ml in fresh medium conditioned by the retroviral producer clone G1MD1 A1.2 prepared as described in Example 2. This medium includes hematopoietic growth factors as specified above plus protamine sulfate at a concentration of 5 ug/ml. Every twelve hours the cells were recovered by centrifugation and resuspended in fresh virus conditioned medium with growth factors and protamine. After 72 hours of incubation in the presence of retroviral vector particles, the cells were recovered by centrifugation, resuspended in DMEM or HBSS containing 2% fetal calf serum and 10 units of heparin per ml, and reinfused into the transplant recipient. During the in vitro culture, the cells expand approximately 10 fold so that $2-4\times10^6$ cells are returned to the animal.

Initially, cells were analyzed after in vitro incubation for evidence of gene transfer and expression. DNA was recovered and subjected to analysis by the polymerase chain reaction methodology using primers (MDR Primer 7, which has the sequence 5'-GCCCACATCATCATGATC-3'p0 (SEQ ID NO:15) and MDR Primer 8, which has the sequence 5'-GTCTCCTACTTTAGTGCT-3' (SEQ ID NO:16)) specific for the human mdr1 coding sequences. Based on comparison to signal intensity obtained with a retroviral producer clone containing a single copy of the retroviral genome, we concluded that 10% of the cells had undergone transduction. The Rhodamine efflux assay hereinabove described was performed confirming that, when compared to a mock infected control sample, 10% of the CD34 selected, transduced cells expressed the mdr1 gene product.

The transplant recipients received daily intravenous fluids, broad spectrum antibiotics, antifungal agents, hyperalimentation solution and blood products as needed to maintain an optimal physiological condition. Daily blood counts and blood chemistries were obtained to monitor recovery. On day 1 following transplantation, granulocyte colony-stimulating factor was given at a dose of 5 ug/kg/day by continuous intravenous infusion. When recovery to a leukocyte count of $1,000-3,000/mm^3$ occurs (day 14–22), blood samples are obtained for detection of the mdr1 gene and its expression.

DNA was purified from the total population of blood leukocytes after lysis of the red cells, and isolation of nuclei from leukocytes. This DNA was analyzed by the polymerase chain reaction methodology using the P7 and P8 primers described above. In the first animal transplanted, approximately 1% of the cells contained the retroviral genome whereas in the second animal 8% of the cells contained the transferred sequences.

It is to be understood, however, that the scope of the present invention is not to be limited to the specific embodiments described above. The invention may be practiced other than as particularly described and still be within the scope of the accompanying claims.

What is claimed is:

1. Isolated DNA or RNA encoding human mdr1 p-glycoprotein wherein said DNA or RNA includes a first sequence:

CAGGTATGC (SEQ ID NO: 1), and a second sequence:

ACATTTTTCCTTCAGG (SEQ ID NO:2), or the RNA equivalent(s) thereof and wherein at least one base of at least one of (SEQ ID NO:1) and (SEQ ID NO:2) or RNA equivalent(s) thereof has been changed to a different base to suppress splicing.

2. The isolated DNA or RNA of claim 1 wherein at least one base in the GT pair in (SEQ ID NO:1) is changed.

3. The isolated DNA or RNA of claim 1 wherein at least one base in the AG pair in (SEQ ID NO:2) is changed.

4. The isolated DNA or RNA of claim 1 wherein said base change is made such that a codon encoding an amino acid is changed to a different codon encoding the same amino acid.

5. The isolated DNA or RNA of claim 4 wherein said codon is AGG in (SEQ ID NO:1) and said codon is changed to AGA.

6. The isolated DNA or RNA of claim 4 wherein said codon is CAG in (SEQ ID NO:2) and said codon is changed to CAA.

7. The isolated DNA or RNA of claim 1 wherein said DNA or RNA has been further mutated to remove a portion of the 5' untranslated region or a portion of the 3' untranslated region.

8. The isolated DNA or RNA of claim 1 wherein at least one base of (SEQ ID NO:1) and at least one base of (SEQ ID NO:2) have been changed to a different base to suppress splicing.

9. The isolated DNA or RNA of claim 8 wherein at least one base in the GT pair in (SEQ ID NO:1) is changed and at least one base in the AG pair in (SEQ ID NO:2) is changed.

10. The isolated DNA or RNA of claim 8 wherein said base changes are made such that a codon in (SEQ ID NO:1) encoding an amino acid is changed to a different codon encoding the same amino acid and a codon in (SEQ ID NO:2) encoding an amino acid is changed to a different codon encoding the same amino acid.

11. The isolated DNA or RNA of claim 10 wherein said codon in (SEQ ID NO:1) is AGG and is changed to AGA and said codon in (SEQ ID NO:2) is CAG and is changed to CAA.

12. The isolated DNA or RNA of claim 8 wherein said DNA or RNA has been further mutated to remove a portion of the 5' untranslated region or a portion of the 3' untranslated region.

13. An isolated modified human mdr1 gene (SEQ ID NO:18) or the RNA equivalent thereof wherein at least one base of (SEQ ID NO:1) at nucleotides 760 to 768 of the wild-type human mdr1 gene (SEQ ID NO:18) or at least one base of (SEQ ID NO:2) at nucleotides 2729 to 2744 of the wild-type human mdr1 gene (SEQ ID NO:18) has been changed to a different base to suppress splicing.

14. The isolated modified human mdr1 gene (SEQ ID NO:18) or RNA equivalent of claim 13 wherein codon 185 of (SEQ ID NO:18) is changed from GTT to GGT, thereby changing Val to Gly in the expressed protein.

15. The isolated modified human mdr1 gene (SEQ ID NO:18) or RNA equivalent of claim 13 wherein at least one base of said (SEQ ID NO:1) and at least one base of said (SEQ ID NO:2) are modified.

16. The isolated modified human mdr1 gene (SEQ ID NO:18) or RNA equivalent of claim 15 wherein codon 185 is changed from GTT to GGT, thereby changing Val to Gly in the expressed protein.

17. A retroviral vector including the DNA or RNA of claim 1.

18. A retroviral vector including the DNA or RNA of claim 8.

19. A retroviral vector including the DNA or RNA of claim 13.

20. A primate cell containing the DNA or RNA of any one of claims 1, 4, 5, 6, 7, 13, or 14.

21. The primate cell of claim 20 wherein said cell is a bone marrow cell.

* * * * *